(12) United States Patent
Smith et al.

(10) Patent No.: US 11,033,901 B2
(45) Date of Patent: Jun. 15, 2021

(54) BIOMARKER DETECTION USING INTEGRATED PURIFICATION-DETECTION DEVICES

(71) Applicant: International Business Machines Corporation, Armonk, NY (US)

(72) Inventors: Joshua T. Smith, Croton on Hudson, NY (US); Benjamin Wunsch, Mt. Kisco, NY (US); Stacey Gifford, Fairfield, CT (US); Sung-Cheol Kim, New York, NY (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 300 days.

(21) Appl. No.: 16/168,228

(22) Filed: Oct. 23, 2018

(65) Prior Publication Data

US 2020/0122144 A1   Apr. 23, 2020

(51) Int. Cl.
*G06T 7/00* (2017.01)
*B01L 3/00* (2006.01)

(52) U.S. Cl.
CPC ...... *B01L 3/502753* (2013.01); *G06T 7/0012* (2013.01); *B01L 2300/0654* (2013.01)

(58) Field of Classification Search
CPC ..... B01L 2200/0663; B01L 2300/0636; B01L 2300/0654; B01L 2300/0877; B01L 2300/0896; B01L 3/502753; G01N 21/6458; G01N 33/00; G06T 7/0012
See application file for complete search history.

(56) References Cited

U.S. PATENT DOCUMENTS

| 9,636,675 B2 | 5/2017 | Astier et al. |
| 9,700,891 B2 | 7/2017 | Smith et al. |
| 9,868,119 B2 | 1/2018 | Astier et al. |

(Continued)

FOREIGN PATENT DOCUMENTS

WO   WO-2012162779 A1 * 12/2012 ........... C12Q 1/6806

OTHER PUBLICATIONS

Yanez-Mo, et al., "Biological properties of extracellular vesicles and their physiological functions," Published online: May 14, 2015, DOI: 10.3402/jev.v4.27066, 62 pages.

(Continued)

*Primary Examiner* — Jennifer Wecker
(74) *Attorney, Agent, or Firm* — Amin, Turocy & Watson, LLP

(57) ABSTRACT

Techniques regarding integrated purification-detection devices for detecting one or more biomarkers are provided. For example, one or more embodiments described herein are directed to an apparatus, comprising a housing and a microfluidic chip contained within the housing. The microfluidic chip comprises a separation unit that separates, using one or more nano deterministic lateral displacement (nanoDLD) arrays, target biological entities having a defined size range from other biological entities included in a biological fluid sample. The microfluidic chip further comprises a detection unit that facilitates detecting presence of one or more biomarkers associated with the target biological entities using one or more detection molecules or macromolecules that chemically reacts with the one or more biomarkers.

23 Claims, 20 Drawing Sheets

(56) References Cited

U.S. PATENT DOCUMENTS

| | | | |
|---|---|---|---|
| 2008/0014632 A1* | 1/2008 | Cunningham | G01N 21/7743 435/288.7 |
| 2014/0080203 A1* | 3/2014 | Wan | G01N 33/558 435/287.2 |
| 2015/0362434 A1* | 12/2015 | Finkelstein | A61B 5/0013 506/9 |
| 2016/0144406 A1 | 5/2016 | Astier et al. | |
| 2016/0320389 A1 | 11/2016 | Astier et al. | |
| 2017/0167981 A1 | 6/2017 | Hu et al. | |
| 2017/0248508 A1* | 8/2017 | Ward | G01N 15/1404 |
| 2018/0080060 A1 | 3/2018 | Gifford et al. | |
| 2018/0080857 A1 | 3/2018 | Gifford et al. | |

OTHER PUBLICATIONS

Wunsch, et al., "Nanoscale lateral displacement arrays for the separation of exosomes and colloids down to 20 nm," Published Online: Aug. 1, 2016 | DOI: 10.1038/NNANO.2016.134, 7 pages.

Woo, et al., "Exodisc for Rapid, Size-Selective, and Efficient Isolation and Analysis of Nanoscale Extracellular Vesicles from Biological Samples," ACS Nano 2017, 11, pp. 1360-1370.

Liu, et al., "Field-Free Isolation of Exosomes from Extracellular Vesicles by Microfluidic Viscoelastic Flows," 9 pages.

Liu, et al., "The Exosome Total Isolation Chip," DOI: 10.1021/acsnano.7b04878, 12 pages.

Im, et al., "Label-free detection and molecular profiling of exosomes with a nano-plasmonic sensor," vol. 32 No. 5 May 2014, doi:10.1038/nbt.2886, 10 pages.

Jeong, et al., "Integrated Magneto-Electrochemical Sensor for Exosome Analysis," ACS Nano 2016, 10, 1802-1809, DOI: 10.1021/acsnano.5b07584, 8 pages.

Salafi, et al., "Advancements in microfluidics for nanoparticle separation," Lab Chip, 2017, 17, 11, DOI: 10.1039/c6lc01045h, 23 pages.

Nge, et al., "Advances in Microfluidic Materials, Functions, Integration and Applications," Chem Rev. Apr. 10, 2013; 113(4): 79 pages, doi:10.1021/cr300337x.

Dang, et al., "Integrated Microfluidic Cooling and Interconnects for 2D and 3D Chips," IEEE Transactions on Advanced Packaging, vol. 33, No. 1, Feb. 2010, 9 pages.

Morton, et al., "Crossing microfluidic streamlines to lyse, label and wash cells," First published as an Advance Article on the web Jul. 23, 2008, DOI: 10.1039/b805614e, 6 pages.

McDonald, et al., "Fabrication of microfluidic systems in poly(dimethylsiloxane)," Electrophoresis 2000, 21, pp. 27-40.

Contreras-Naranjo, et al., "Fabrication of microfluidic systems in poly(dimethylsiloxane)," Lab Chip, 2017, DOI: 10.1039/C7LC00592J, 50 pages.

Huang, et al., "Continuous Particle Separation Through Deterministic Lateral Displacement," Published online Apr. 15, 2004; DOI:10.1126/science.1095191, 4 pages.

O'Kennedy, "Applications of Antibodies in Microfluidics-based Analytical Systems: Challenges and Strategies for Success," 2018 J. Micromech. Microeng. in press https://doi.org/10.1088/1361-6439/aab225, 33 pages.

Thery, et al., "Isolation and Characterization of UNIT 3.22 Exosomes from Cell Culture Supernatants and Biological Fluids," Current Protocols in Cell Biology (2006) 3.221-322.29, 29 pages.

De Toro, et al., "Emerging roles of exosomes in normal and pathological conditions: new insights for diagnosis and therapeutic applications," May 2015 | vol. 6 | Article 203, 12 pages.

Shurtleff, et al., "Y-box protein 1 is required to sort microRNAs into exosomes in cells and in a cell-free reaction," eLife 2016;5:e19276. DOI: 10.7554/eLife.19276, 23 pages.

* cited by examiner

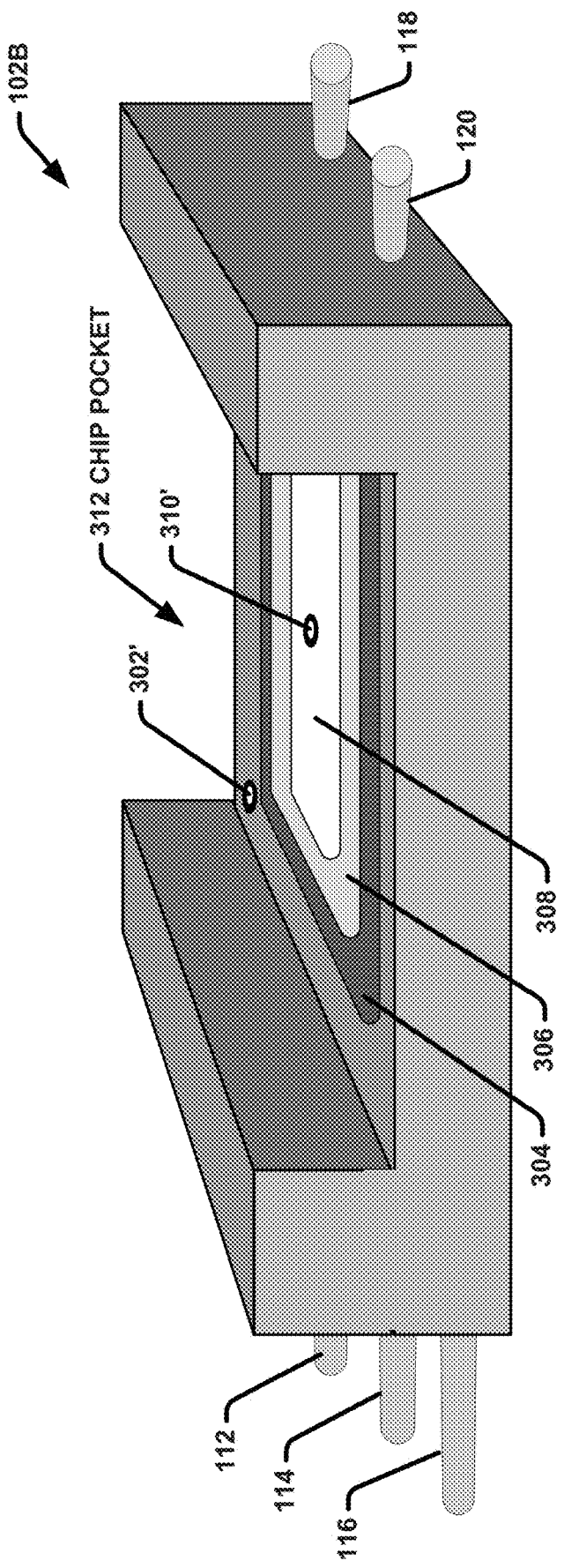

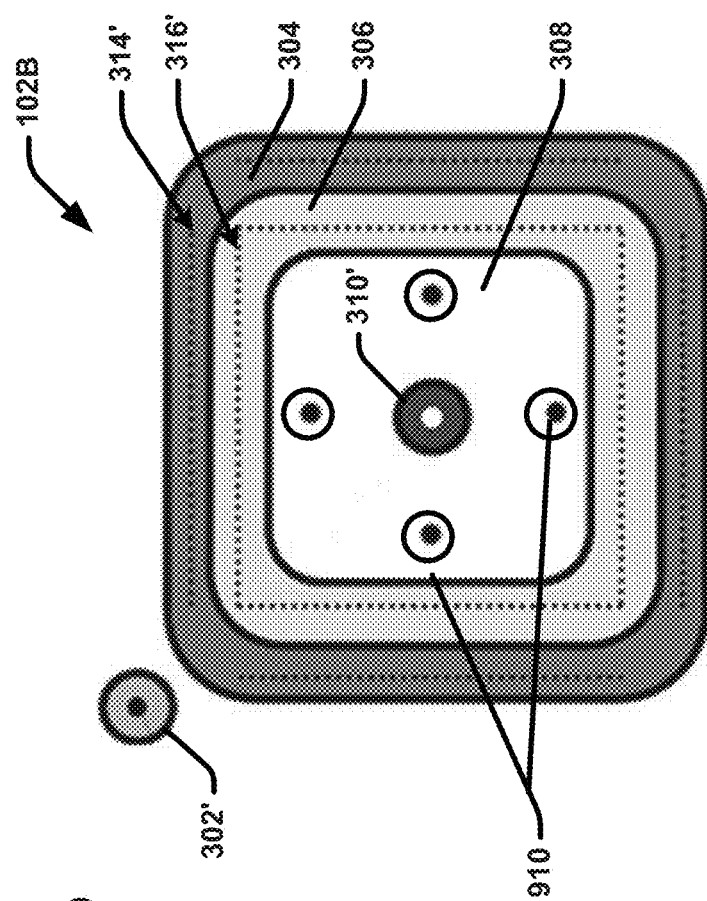
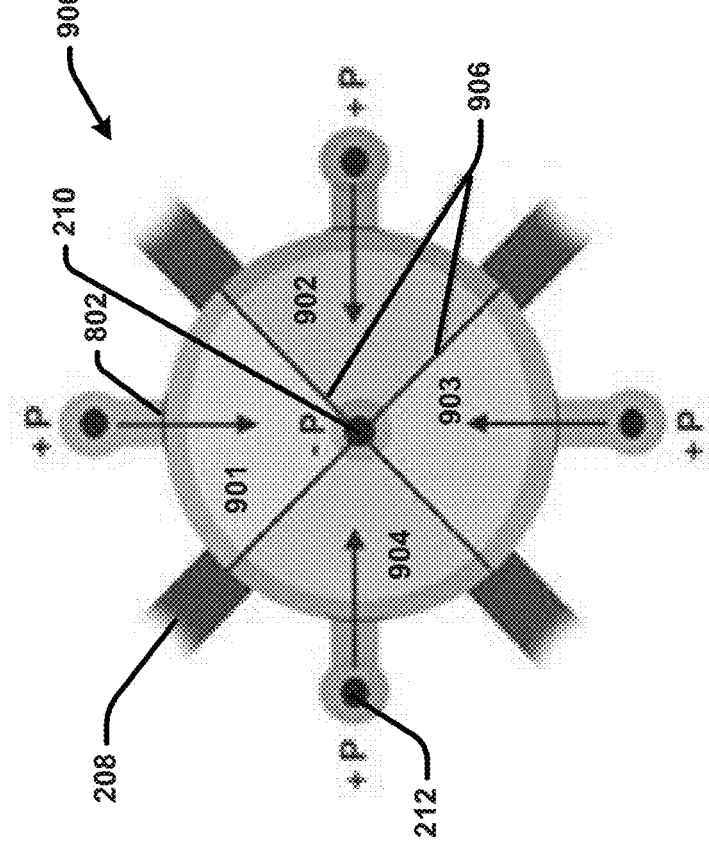
FIG. 9B
FIG. 9A

BIOMARKER DETECTION USING INTEGRATED PURIFICATION-DETECTION DEVICES

BACKGROUND

The subject disclosure relates to integrated purification-detection devices for detecting one or more biomarkers, and more specifically, to integrating lateral deterministic displacement arrays for particle purification and one or more sensor arrays for biomarker detection onto a single microfluidic chip.

Technologies capable of detecting the presence of biomarkers are ubiquitous in biochemistry and a necessary element of diagnostic devices in healthcare. Common methods of detection, such as enzyme-linked immunosorbent assays (ELISAs), utilize high-affinity interactions between antibodies and their target epitope to achieve chemical specificity in detecting a particular analyte. One exemplary application of this method of revealing chemical specificity is targeting the epitopes of exosomes. Exosomes are extracellular vesicles (EVs) ranging in size from 30-150 nanometers (nm) found in minimally invasive and completely non-invasive biological fluids, or liquid biopsies, such as blood, urine, saliva, etc. Exosomes have emerged as a promising class of biomarkers for studying and identifying various disease conditions. These EVs contain a rich set of genetic information, including tumor-specific proteins, micro ribonucleic acid (microRNA), messenger RNA (mRNA), and deoxy ribonucleic acid (DNA), that can individually and/or collectively provide a glimpse into the health state of an individual at the sub-cellular level. To extract meaningful information from these nanoscale prognosticators first requires the ability to isolate them from a complex biological fluid. Once they are extracted, some form of biochemical analysis or genetic sequencing is needed to detect presence of biomarkers. Both the extraction and detection processes at present are cumbersome, costly, and impractical for frequently running a diagnosis to catch a disease at an early stage or for monitoring a patient's response to a particular treatment.

Focusing on the first requirement, the extraction piece, many standard biochemistry methods have been applied to isolate exosomes, each with its own set of drawbacks, and, in general, the community is actively seeking for better solutions to the sample preparation problem of EVs. The most common methods currently employed for the task include ultracentrifugation (UC), filtration, precipitation, immunoaffinity-based capture, nano deterministic lateral displacement (nanoDLD), Exodisc, viscoelastic flows, and exoTIC.

Ultracentrifugation (UC) exploits size differences between cells, EVs, and proteins to isolate these materials from each other using progressively higher spin speeds with intermediate extraction protocol. Major drawbacks are high spin speeds that can impact EV quality and long run times (around 5 hours). UC is also a manual, batch process often resulting in lower exosome recovery and less than optimal EV quality. Filtration isolation techniques employ membrane filters, such as polyvinylidene difluoride (PVDF) or polycarbonate filters, to sieve cells and large EVs from biological samples. Filtration is sometimes coupled with ultracentrifugation to further separate exosomes from proteins. These types of multistep arrangements require a bulky centrifuge or vacuum system, use large sample volumes (30-100 milliliters (mL)), require batch processing, and typically result in poor yields due to clogging.

Several precipitation kit-based solutions have emerged to circumvent the need for UC, including EXOEASY®, EXOSPIN®, EXOQUICK® exosome precipitation, TOTAL EXOSOME ISOLATION REAGENT®, and/or PURE-EXO®, to name a few. These products use special reagents to induce precipitation of exosomes, such as polyethylene glycol (PEG) based additives. These kits typically suffer from unacceptable purity due to polymer contamination, making downstream analysis difficult. These precipitation kits are also often limited to small, batched sample volumes.

The immunoaffinity-based capture isolation method specifically targets exosomes from a complex biological fluid using, for example, tetraspanin proteins such as CD81 found on the surface of exosomes or markers specific to the exosome's cell of origin to isolate them. A common technique utilizes antibody coated magnetic beads to capture exosomes that contain specific markers from bodily fluids. These methods are expensive, relying on specific antibodies that can vary batch to batch and suffer from stability issues. Thus, while these methods allow specific subpopulations of exosomes to be isolated, the cost of antibodies makes them generally unsuitable for isolating exosomes from large quantities of biological samples.

In light of the inherent drawbacks surrounding the above-mentioned isolation standards, exploration of new solutions that can provide a route toward a simple, inexpensive, automated, and rapid EV isolation techniques have been reported in literature, including for example, lab-on-a-chip based approaches. Exemplary techniques within this realm include nanoDLD, Exodisc, viscoelastic flows, and ExoTIC. NanoDLD refers to a technique wherein deterministic lateral displacement (DLD) technology is shrunk to the nanoscale, demonstrating the ability to subfractionate exosome populations with tens of nanometers resolution in a continuous flow system (no batch processing) with a theory of operation. However, current nanoDLD techniques can only process very low sample volumes at low throughput rates (e.g., about 0.2 microliters (µLs) per hour (hr)). Exodisc is a lab-on-a-disc separation technique presented in H.-K. Woo, et al., ACS Nano, vol. 11, pp. 1360, 2017. The Exodisc technique integrates two on-disc nanofilters that allow fully automated and label-free enrichment of EVs in the size range of 20-600 nanometers (nm) within 30 minutes using a tabletop-sized centrifugal microfluidic system. Although the Exodisc technique have reportedly demonstrated high yields (e.g., greater than 95% recovery of EVs from cell culture and greater than a 100-fold higher concentration of mRNA as compared with UC), the discs employed are large and costly. In addition, sample processing is batched rather than continuous flow, and subfractionation of exosomes is not demonstrated or straightforwardly applicable.

Viscoelastic flow techniques have been used to isolate exosomes from cell culture media and serum in a continuous flow, field-free, and label-free manner using an additive polymer (poly-oxyethylene or PEO) to control the viscoelastic forces exerted on nanoscale EVs. As reported in C. Liu, et al., ACS Nano, vol. 11, pp. 6968, 2017, viscoelastic flow techniques have demonstrated a separation purity greater than 90% with a recovery of greater than 80% and a throughput of 200 µL/hr. However, these techniques also suffer from disadvantages. In particular, viscoelastic flow devices are large (and thus more cumbersome and costly), requiring channels of 32 millimeters (mm) in length to achieve lateral resolution of particle streams (plus space for input/outports), and although isolation of 100 nm and 500 nm particles sizes have been shown, this size selectivity does not lend itself to exosome fractionation.

The exosome total isolation chip (ExoTIC) filtration technique is another exosome isolation technique reported in F. Liu, et al., *ACS Nano*, vol. 11, pp. 10712-10723, 2017. ExoTIC employs a filtration arrangement to achieve EV yields from 4 to 1000 fold higher than UC using a low protein binding filter membrane from track-etched polycarbonate and a syringe pump driver at flowrates up to 30 mL/hr shown on 6 parallel syringes. A buffer wash step allows for EV purification from smaller contaminates. Sub-fractionation is also demonstrated by staging filters down to the nanoscale and exosomes from specific cell lines are analyzed in terms of their size distribution. However, since filtration and purification are inherently sequential processes, Exotic is a batch process requiring over 2 hours to perform a sample preparation. In addition, nanoparticle tracking analysis (NTA) performed on ExoTIC subfractionated EV populations does not indicate strong control of fractionated sizes, which calls into question run-to-run reliability.

Exosome detection and molecular profiling of exosomes presents an added challenge for exosome-based cancer diagnostics. Few technologies have arisen that attempt to tackle this problem. One technique described in H. Im, et al., *Nat. Biotechnol.*, vol. 32, pp. 490-495, 2014, includes a nanoplasmonic exosome (nPLEX) assay, which uses transmission surface plasmon resonance through periodic nanohole arrays functionalized with antibodies to profile the surface proteins of exosomes as well as proteins present in exosome lysates. This technique was successful at identifying exosomes derived from ovarian cancer cells by their expression of CD24 and EpCAM with 100 times the sensitivity of an ELISA, and the exosomal and cellular protein profiles showed excellent correlation. However, upfront sample preparation was required for the nPLEX device to obtain a clean signal using standard UC or filtration. Another technique has been developed that uses an integrated magneto-electrochemical sensor for exosome (iMEX) analysis. (See S. Jeong, et al., *ACS Nano*, vol. 10, pp. 1802-1809, 2016). The iMEX technique involves enriching exosomes directly from blood and profiling them for molecular information. The platform uses magnetic selection and electrochemical enrichment to isolate cell-specific exosomes from complex media and achieved high sensitivity through magnetic enrichment and enzymatic amplification to detect these markers electrically. This technique however requires magnetic beads bearing horseradish peroxidase (HRP) labels to isolate the exosomes and produce a signal. In addition, off-platform sample preparation is required for each biomarker along with manual loading of the prepared sample onto each electrode.

SUMMARY

The following presents a summary to provide a basic understanding of one or more embodiments of the invention. This summary is not intended to identify key or critical elements or delineate any scope of the particular embodiments or any scope of the claims. Its sole purpose is to present concepts in a simplified form as a prelude to the more detailed description that is presented later. In one or more embodiments described herein, systems, apparatuses, and/or methods are provided that relate to integrated purification-detection devices for detecting one or more biomarkers.

In accordance with various embodiments, an apparatus is provided that comprises a housing and a microfluidic chip contained within the housing. The microfluidic chip comprises a separation unit that separates, using one or more nanoDLD arrays, target biological entities having a defined size range from other biological entities included in a biological fluid sample. The microfluidic chip further comprises a detection unit that facilitates detecting presence of one or more biomarkers associated with the target biological entities using one or more detection molecules or macromolecules that chemically reacts with the one or more biomarkers. In some implementations, the biological entities comprise exosomes. The biological entities can also include other biological molecules and macromolecules ranging in size from 10.0 nm to 200 nm, viruses, DNA sequences, RNA sequences and the like. In some implementations, the one or more detection molecules or macromolecules comprise an antibody or aptamer that binds with a target epitope of the one or more biomarkers.

In various implementations, the detection unit can comprise a sensing element, wherein a surface of the sensing element is coated with the one or more detection molecules or macromolecules. With these implementations, the detection molecules or macromolecules can chemically react with the one or more biomarkers by binding to the one or more detection molecules or macromolecules. In some implementations, based on the binding, the one or more detection molecules or macromolecules generate a visual signal, such as a florescent signal. The sensing element can also comprise a signal enhancing structure selected from a group consisting of a photonic grating structure, a photonic pillar array structure, an optoelectrical structure, and a plasmonic structure. In one or more implementations, a portion of the housing formed adjacent to the sensing element is transparent or partially transparent and enables visual observation of the fluorescent signal.

The microfluidic chip can further comprise at least one conduit from the separation unit to the detection unit that facilitates passage of buffer fluid comprising the target biological entities, as separated from the other biological entities, from the separation unit to the detection unit. At least one inlet can be included on the microfluidic chip through which the buffer fluid passes from the conduit to the surface of the sensing element. In some implementations, the detection unit further comprises a blocking element formed at an interface between the surface of the sensing element and the at least one inlet. The blocking element can inhibit reverse flow of one or more reacted or unreacted molecular complexes (e.g., antibody/exosome complexes) from the surface of the sensing element through the at least one inlet, wherein the one or more reacted molecular complexes are formed as a result of a chemical reaction between the one or more detection molecules or macromolecules and the one or more biomarkers (e.g., an epitope on the surface of the exosomes). The microfluidic chip can further comprise at least one outlet from which the buffer fluid and unreacted portions of the target biological entities that fail to chemically react with the one or more detection molecules or macromolecules, are excreted from the detection unit.

In some implementations, the microfluidic chip further comprises at least one inlet via which solution comprising the one or more detection molecules or macromolecules are injected into the detection unit to coat the surface of the sensing element. In addition, in order to facilitate simultaneous detection of a plurality of biomarkers, the detection unit can comprise two or more separate detection chambers, wherein respective chambers of the two or more separate detection chambers comprise different types of detection molecules or macromolecules of the one or more detection molecules or macromolecules. In this regard, the different types of detection molecules or macromolecules can chemically react with different types of biomarkers.

In another embodiment, a method is provided that comprises isolating target biological entities (e.g., exosomes) having a defined size range from other biological entities included in a biological fluid sample using a separation unit comprising one or more nanoDLD arrays formed on a microfluidic chip, thereby resulting in isolated target biological entities. The method further includes driving flow of a buffer fluid comprising the isolated target biological entities through a conduit of the microfluidic chip from the separation unit to a sensing element formed on the microfluidic chip, and facilitating detection of presence of one or more biomarkers associated with the isolated target biological entities based on whether a detectable signal is generated by the sensing element in response to the driving.

For example, the sensing element can comprise one or more detection molecules or macromolecules, and the detectable signal can comprise a reaction signal that is indicative of a chemical interaction between the one or more detection molecules or macromolecules and the one or more biomarkers. For instance, the chemical reaction can include a reaction selected from a group consisting of a covalent bonding reaction, an electrostatic interaction, a hydrophobic interaction, an antibody-epitope reaction, an aptamer-epitope reaction, a protein-protein interaction, a protein-small molecule interaction, a polymerization reaction, a complementarity reaction, a complementary DNA strand hybridization interaction, and a complementary RNA strand hybridization interaction. In some implementations, prior to the driving, the method can comprise. Functionalizing a surface of the sensing element with the one or more detection molecules or macromolecules, wherein the functionalizing comprises injecting a solution comprising the one or more detection molecules or macromolecules into a chamber enclosing the surface of sensing element via at least one injection inlet of the microfluidic chip.

In some implementations of the subject method, the detectable signal comprises a visual signal. With these implementations, the method can further comprise determining whether the detectable signal is generated using a microscope positioned adjacent the sensing element. The method can also include capturing, by a device operatively coupled to a processor, image data of the sensing element in association with the driving, and determining, by the device, whether the visual signal is generated based on the image data.

In another embodiment, an apparatus is provided comprising a housing and a microfluidic chip contained within the housing. The microfluidic chip comprises a separation unit that separates, using one or more nanoDLD arrays, exosomes from other biological entities included in a biological fluid sample, resulting in isolated exomes. The microfluidic chip further comprises a detection unit that facilitates detecting presence of different biomarkers located on or within with the exosomes using different detection entities that respectively chemically react with the different biomarkers, wherein the different detection entities are selected from a group consisting of molecules and macromolecules, and at least one channel from the separation unit to the detection unit that facilitates flow of a buffer solution comprising the isolated exomes to the detection unit. In some implementations, the detection unit comprises different chambers that respectively detect presence of a different type of biomarker of the different types of biomarkers, and wherein the different chambers are respectively coated with a different detection entity of the different detection entities.

In one or more additional embodiments, a system is provided comprising a microfluidic chip contained within a housing, wherein the microfluidic chip comprises a separation unit that separates, using one or more nanoDLD arrays, target biological entities having a defined size range from other biological entities included in a biological fluid sample, resulting in isolated target biological entities. The microfluidic chip further comprises a detection unit that facilitates detecting presence of one or more biomarkers associated with the isolated target biological entities using one or more detection molecules or macromolecules that chemically react with the one or more biomarkers, and at least one channel from the separation unit to the detection unit that facilitates flow of a buffer solution comprising the isolated target biological entities to the detection unit. The system further comprises an imaging device (e.g., a microscope, a camera, etc.) that captures image data in association with flow of the buffer solution to the detection unit and contact of the buffer solution with the one or more detection molecules or macromolecules. In some implementations, the system further comprises a memory that stores computer executable components, and a processor that executes the computer executable components stored in the memory. The computer executable components can comprise an analysis component that evaluates the image data to determine biomarker information regarding the presence of the one or more biomarkers. The computer executable components can also comprise a diagnosis component that determines diagnostic information regarding a medical condition of a patient from which the biological fluid is sampled from based on the biomarker information.

In yet another embodiment, a method is provided that comprises isolating target biological entities having a defined size range from other biological entities included in a biological fluid sample using a separation unit comprising one or more nanoDLD arrays, thereby resulting in isolated target biological entities, wherein the separation unit is formed on a microfluidic chip contained within a housing. The method further comprises, driving flow of a buffer fluid comprising the isolated target biological entities through a conduit of the microfluidic chip from the separation unit to a sensing element formed on the microfluidic chip, wherein the sensing element generates a visual signal in response to detection of presence of one or more defined biomarkers associated with the target biological entities. The method further comprises capturing image data of the detection unit in association with the driving.

BRIEF DESCRIPTION OF THE DRAWINGS

FIG. 3A presents a 3D view of an example bottom plate of housing that couples with a microfluidic chip to facilitate on-chip particle purification and biomarker detection functionality in accordance with one or more embodiments described herein.

FIG. 9A illustrates an enlarged view of another example detection unit of an example microfluidic chip that integrates on-chip particle purification and biomarker detection functionality in accordance with one or more embodiments described herein.

FIG. 9B presents an orthogonal, 2D, perspective view of another example housing that couples with a microfluidic chip to facilitate on-chip particle purification and biomarker detection functionality in accordance with one or more embodiments described herein.

DETAILED DESCRIPTION

Figure 1A:
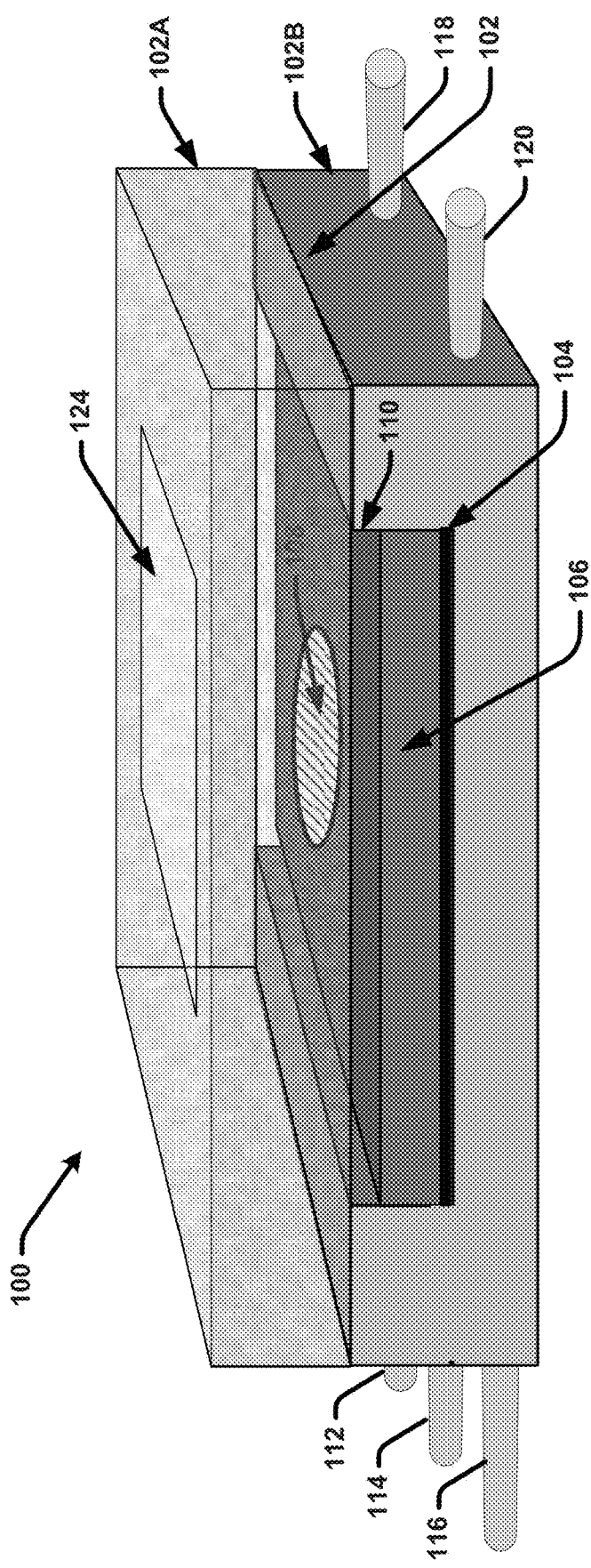
FIGS. 1A and 1B illustrate a diagram of an example, non-limiting separation-purification apparatus that integrates on-chip particle purification and biomarker detection functionality in accordance with one or more embodiments described herein.

The following detailed description is merely illustrative and is not intended to limit embodiments and/or application or uses of embodiments. Furthermore, there is no intention to be bound by any expressed or implied information presented in the preceding Background or Summary sections, or in the Detailed Description section.

Various embodiments described herein are directed to microfluidic chip devices and systems that integrate biomarker detection together with upstream isolation and purification of biological entities, all on a single chip, providing a powerful self-contained, and portable solution to biochemical identification of disease-related biomarkers. The integrated purification-detection devices can be tailored to isolate and detect biomarkers associated with various types of biological particles, including exosomes, as well as viruses and other biological entities. In one or more embodiments, the microfluidic chip comprises as sensing element that provides for real-time detection of one or many biomarkers located downstream of a continuous flow isolation and purification separation element that is also located on the microfluid chip. By integrating an upstream separation element with the sensing element, the noise floor of the sample is minimized to enhance sensitivity by removing background contaminates and larger unwanted material, such as cellular debris and multi-vesicular bodies (MBVs).

The separation element can employ an arrangement of multiplexed lateral deterministic displacement (DLD) arrays, (e.g., nanoDLD arrays) for a buffer exchange of target biomolecules (e.g., exosomes) from an input sample with smaller contaminants, such as small molecules, proteins, and salts, exiting a common set of waste outlets. The nanoDLD arrays can be configured to bump or otherwise direct purified target biological entities into the portion of the buffer medium that flows into a common bus toward the downstream sensing element. In various embodiments, the sensing element can provide for detecting presence of one or more biomarkers present on the surface of the purified target biomolecules via chemical specificity between the one or more biomarkers and another chemical coated on the surface of the sensing element. For example, the sensing element can be coated with antibodies having a chemical specificity for a known epitope that may be present on the surface of isolated exosomes. In some implementations, the sensing element can incorporate a plurality of different antibodies that provide for simultaneous detection of two or more biomarkers. Simultaneous detection of multiple markers allows for fast, effective diagnosis of disease, such as certain forms of cancer. However, the sensing element biomarker detection methods may be more broadly extended to any specific chemical or biochemical interaction between two molecules or macromolecules, can be naturally occurring or synthetic and can be a permanent covalent linkage or a reversible bond (e.g., electrostatic interactions, hydrophobic interactions, complementarity, etc.).

In various exemplary embodiments, the sensing element can be located at or near the center of the chip and provide for optical readout of chemical reactions indicative of biomarker presence. For example, the purified sample can flow from the common bus mover the sensing element, which can include a signal-enhancing element such as a photonic grating, an optoelectrical element or plasmonic structure, coated with antibodies or aptamers known to bind with target epitopes or surface markers. For instance, the sensing element can be configured to detected chemical reactions that produce a fluorescent signal that is observable with fluorescence microscopy, and therefore manually detectable by eye or through software to automate the process. Accordingly, the sensing element can provide for real-time monitoring and diagnosis of a particular disease condition.

In one or more embodiments, the disclosed microfluidic chip can be coupled to a housing to facilitate a real-time exosome separation and biomarker detection process. For example, one exemplary process can include loading (e.g., pipetting) several fluids into various reservoirs onto the housing containing a microfluidic chip. The fluids include a biological sample (e.g., urine, blood, saliva, etc.), a buffer, and one or more fluids containing antibody or aptamer chemistries for surface functionalization of all or dedicated parts of the on-chip sensing element. A pressure-driven can be used to first drives the antibody or aptamer containing fluids onto the sensing element to functionalize the surface for immunocapture of exosomes containing certain target surface markers. Next, the biological sample and buffer can be pressure driven onto the chip where exosomes are harvested and purified using the nano-DLD arrays of the detection unit, and then captured on the downstream sensing element for detection and analysis using fluorescence microscopy, either manually by an operator or using a software analysis program.

In this regard, the subject integrated purification-detection devices and systems provide an all-in-one solution for sample preparation from complex patient fluids together with detection of multiple surface markers all on a single chip. The disclosed exosome isolation and biomarker detection devices provide a uniquely powerful, self-contained, and portable solution to biochemical identification of disease-related exosomal cohorts for biomarker discovery and diagnostic applications. Thus, the technology provides a means of semi-automating the biomarker discovery process as well as aids in rapid sample screening that can potentially be performed at the clinic.

As used herein, the term lab-on-a-chip (LOC) can refer to one or more devices that can integrate one or more laboratory functions onto an integrated circuit (e.g., a semiconductor substrate structure) to achieve autonomous screening of one or more samples. LOCs can utilize microelectromechanical systems and/or microfluidic systems to facilitate screening the one or more samples. One of ordinary skill in the art will recognize that a LOC devices can range in size from, for example, one or more square millimeters to one or more square centimeters. One or more embodiments can utilize microfluidics in a LOC device to detect one or more target biomarkers, wherein the biomarkers can be indicative of various traits (e.g., physical properties) and/or health conditions (e.g., diseases). Thus, in some embodiments, the one or more integrated purification-detection devices described herein can be considered LOC devices that can facilitate biomarker detection, wherein the one or more LOC devices can be operated quickly (e.g., near instantaneously), in a variety of locations (e.g., at an entity's home), and without the typical need for specialized laboratory equipment.

As used herein the term deterministic lateral displacement (DLD) can refer to one or more microfluidic techniques that can size fractionate a polydisperse suspension of molecules through the use of one or more arrays of obstacles. For example, DLD arrays can laterally displace target molecules within a sample stream based on size. Further, DLD arrays can comprise a plurality of pillars arranged in a lattice structure. Rows of pillars comprising the lattice structure can be positioned offset of each other at a defined angle, and pillars can be separated from each other by a defined gap size. The defined angle and/or gap size can facilitate displacement of one or more molecules of a target size range comprised within a stream flowing through the DLD array.

As used herein the term nanoDLD array can refer to a DLD array that can be characterized by one or more dimensions ranging from greater than or equal to 1 nanometer (nm) and less than or equal to 999 nm. For example, a nanoDLD array can be a DLD array characterized by a gap size (e.g., a distance between adjacent pillars comprised within the lattice structure) of greater than or equal to 1 nm and less than or equal to 999 nm (e.g., greater than or equal to 25 nm and less than or equal to 235 nm). In one or more embodiments, a nanoDLD array can facilitate displacement of exosomes, viruses, and other biomolecules or micromodules of various sizes (e.g., from 1 nm to 999 nm). In some implementations, the nanoDLD arrays described herein can also isolate genetic code sequences that can be characterized as having an exemplary length ranging from, but not limited to, greater than or equal to 25 base pairs (bp) and less than or equal to 200 bp.

As used herein, unless otherwise specified, terms such as on, overlying, atop, on top, positioned on, or positioned atop mean that a first element is present on a second element, wherein intervening elements may be present between the first element and the second element. As used herein, unless otherwise specified, the term directly used in connection with the terms on, overlying, atop, on top, positioned, positioned atop, contacting, directly contacting, or the term direct contact, mean that a first element and a second element are connected without any intervening elements, such as, for example, intermediary conducting, insulating or semiconductor layers, present between the first element and the second element. As used herein, terms such as upper, lower, above, below, directly above, directly below, aligned with, adjacent to, right, left, vertical, horizontal, top, bottom, and derivatives thereof shall relate to the disclosed structures as oriented in the drawing figures.

One or more embodiments are now described with reference to the drawings, wherein like referenced numerals are used to refer to like elements throughout. In the following description, for purposes of explanation, numerous specific details are set forth in order to provide a more thorough understanding of the one or more embodiments. It is evident, however, in various cases, that the one or more embodiments can be practiced without these specific details. Further, it is to be understood that common cross-hatching and/or shading depicted across the drawings can represent common features, compositions, and/or conditions described herein in accordance with one or more embodiments.

Figure 1B:
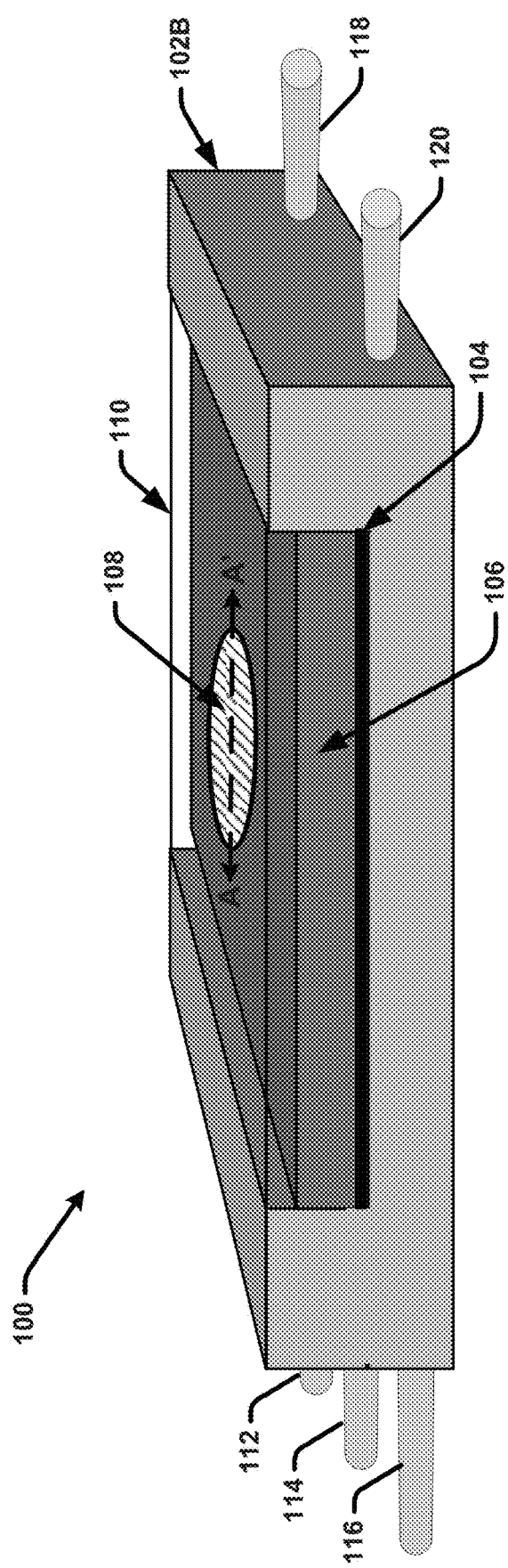

FIGS. 1A and 1B illustrates a diagram of an example, non-limiting, separation-purification apparatus 100 that integrates on-chip particle purification and biomarker detection functionality in accordance with one or more embodiments described herein. As shown in FIG. 1A, the separation-purification apparatus 100 comprises a microfluidic chip 106 provided within a housing 102. The housing is composed of a top plate 102A and a bottom plate 102B. FIG. 2B depicts the separation-purification apparatus 100 with the top plate 102A removed. In various embodiments, the housing 102 can be or correspond to a flow cell or other form of packaging that houses the microfluidic chip 106. For example, in some embodiments, the top plate 102A and the bottom plate 102B can be physically coupled to one another (e.g., via one or more screws or another suitable attachment mechanism) with the microfluidic chip 106 sandwiched therebetween. In the embodiment shown, the top plate 102A is transparent or semitransparent. For example, the top plate 102A can be formed of a clear acrylic plastic, glass, or another suitable material. The bottom plate 102B can also be formed with a transparent or semitransparent material, such as clear acrylic plastic, glass or another suitable material. In other embodiments, the bottom plate 102B can be formed with a non-transparent material, such as silicon or another material in which microchannels, reservoirs, vias, etc., can be fabricated thereon and/or therein.

The microfluidic chip 106 comprises a substrate material with a plurality of elements formed on or within the substrate material that facilitate on-chip particle filtration and biomarker detection. For example, in some embodiments, the microfluidic chip 106 can comprise a silicon substrate with elements formed therein and/or thereon using various semiconductor fabrication techniques. Other suitable materials for the microfluidic chip 106 can include glass, plastic, or a combination thereof. The elements formed on and/or within the microfluidic chip 106 can include a separation unit that includes one or more DLD arrays and/or nanoDLD configured to separate particles of interest (e.g., exosomes) from other particles included in a biological fluid sample. The biological fluid sample can include for example (but is not limited to), a blood sample, a urine sample, a tissue sample, a saliva sample, a plasma sample, a cell culture medium, an in vitro sample, a plant sample, a food samples, a combination thereof, and/or the like. The microfluidic chip 106 further includes a detection unit that facilitates detecting one or more biomarkers located on or within the particles of interest using a sensing element 108. For example, in one or more embodiments, the sensing element 108 can be coated with one or more detection molecules or macromolecules configured to chemically react with the one or more biomarkers. In accordance with theses embodiments, the detection unit can facilitate flowing solution comprising the isolated particles of interest over the sensing element 108. If the one or more biomarkers are present, the one or more detection molecules or macromolecules will chemically react with the biomarkers and produce some form of detectable signal (e.g., a visual signal) that can be read from the sensing element 108. The microfluidic chip 106 further includes a microfluidic busing network consisting of a plurality of microchannels, busses, vias and/or reservoirs formed on or within the microfluidic chip. The microfluidic bussing network facilitates transporting fluid streams between the separation unit, the detection unit, and other elements present on or within the microfluidic chip 106.

As shown in FIG. 1A, the top plate 102A can include a window region 124 formed on or within the top surface of the top plate 102A. This window region 124 can comprise glass or another transparent material (e.g., in implementations in which the material employed for the top plat 102 is semitransparent) that facilitates clearly visualizing the sensing element 108 of the microfluidic chip 106. For example, in some implementations, the window region 124 can be formed with transparent glass and the remainder of the top plate 102A can be formed with transparent or semitransparent acrylic plastic. The window region can be formed in an area of the top plate that is aligned with the sensing element 108 when the top plate 102A is attached to the bottom plate 102B. In some embodiments, (as shown in FIG. 1A and more clearly shown in FIG. 1B), a capping layer 110 can be formed on the top surface of the microfluidic chip 110. The capping layer 110 can comprise a transparent material (e.g., glass, acrylic plastic, etc.) that provides for fluidically sealing the microfluidic elements formed on the top surface of the microfluidic chip 110.

Figure 2A:
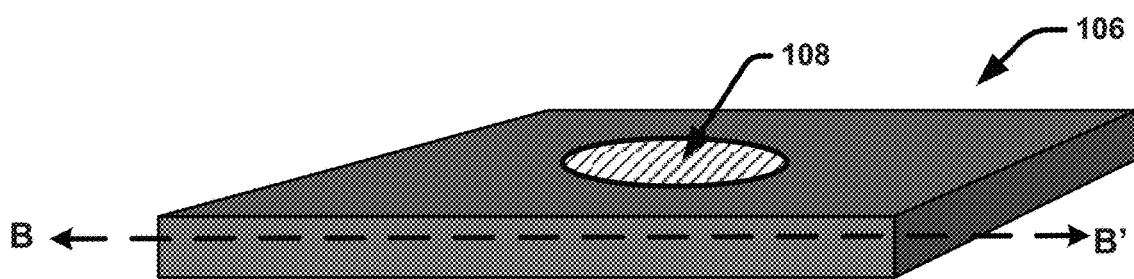
FIG. 2A presents a three-dimensional (3D) view of an example microfluidic chip that integrates on-chip particle purification and biomarker detection functionality in accordance with one or more embodiments described herein.
Figure 2B:
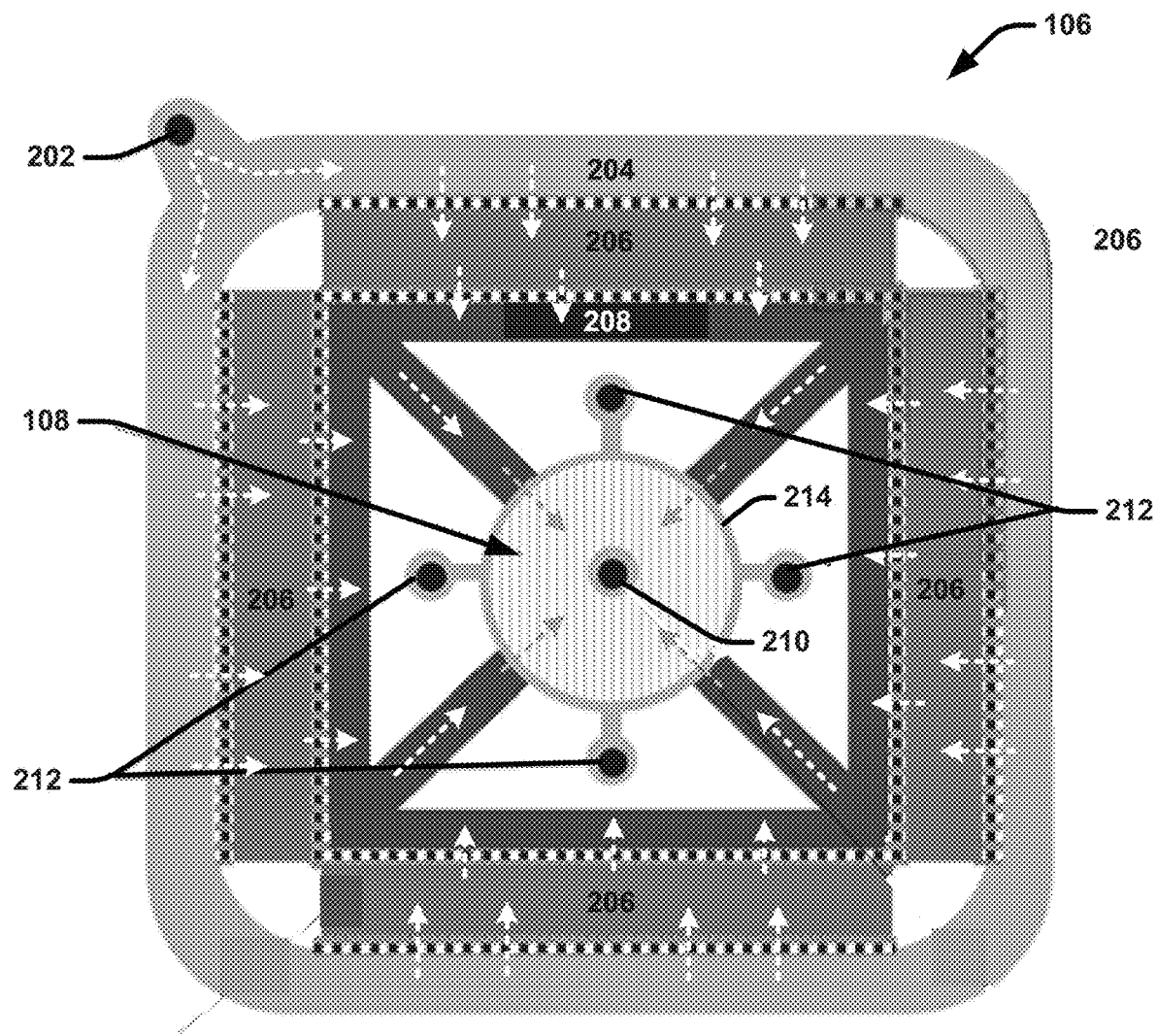
FIG. 2B presents an orthogonal, two-dimensional (2D), perspective view of an example microfluidic chip that integrates on-chip particle purification and biomarker detection functionality in accordance with one or more embodiments described herein.

FIG. 2A presents an example 3D view of microfluidic chip 106 as separated from separation-purification apparatus housing in accordance with one or more embodiments described herein. In the embodiment shown, the capping layer 110 is also removed. FIG. 2B presents an orthogonal, 2D, perspective view of microfluidic chip 106 taken along axis B-B' shown in FIG. 2A, in accordance with one or more embodiments described herein. Repetitive description of like elements employed in respective embodiments is omitted for sake of brevity.

As shown in FIG. 2B, the microfluidic chip 106 can include a circular architecture with several elements formed around the sensing element 108 provided at or near the center of the chip. In particular, (shown in light grey), the microfluidic chip 106 can include an inlet bus 204 formed around an outer perimeter area of the chip and fluidically coupled to a global inlet via 202. For example, the inlet bus 204 can be etched or otherwise formed within a portion of the thickness of the chip. In some implementations, the inlet bus 204 can be etched deeper than other fluidic channels and/or elements formed within the thickness of the chip. For example, in some implementations, the base of the inlet bus 204 can be located 100 μm (or greater) from the bottom surface of the microfluidic chip (e.g., the surface opposite the capping layer 110), without penetrating the bottom surface of the microfluidic chip. The global inlet via 202 can however penetrate through the bottom surface of the microfluidic chip to facilitate receiving and transporting fluid therethrough and into the inlet bus 204. For example, in various embodiments, the inlet bus 204 can be configured to receive biological sample fluid introduced through the global inlet via 202, and distribute the biological sample fluid evenly, (or substantially evenly) throughout the inlet bus 204 (e.g., in the direction shown via the dashed arrows extending from the global inlet via 202).

The microfluidic chip 106 further includes a separation unit 206 formed around the sensing element 108 and within the perimeter of the inlet bus 204. For example, in the embodiment shown, the separation unit 206 is divided into four segments respectively arranged in ring shape (or more accurately, a rectangular shape) within the perimeter of the inlet bus. However, it should be appreciated that the specific shape or geometrical configuration of the separation unit 206 can vary. In the embodiment shown, the separation unit 206 encompasses the alternating black and white checkered lines formed parallel to one another, as well as the dark grey region formed in between them. As discussed in greater detail, the dark grey region of the separation unit 206 can comprise a plurality of DLD or nanoDLD arrays configured to separate target particles of a particular size range from other particles included in the biological sample fluid, and the respective checked lines can correspond to inlet and outlet vias through which fluid passes into and out of the DLD or nanoDLD array.

For example, in some implementations, the first or outermost checkered line provided at the interface between the inlet bus 204 and the DLD or nanoDLD region (e.g., the dark grey region), can include a plurality of openings through which the biological fluid sample can flow from the inlet bus 204 and into the DLD or nanoDLD array, (e.g., in the direction shown by the dashed arrows). In some implementations, the first checkered line can also include a plurality of second inlet vias through which another fluid, such as a buffer fluid, can be introduced. For example, as discussed in greater detail infra, as the biological fluid and the buffer fluid can simultaneously flow through the DLD or nanoDLD arrays, the particles of interest can be bumped into or otherwise captured in first streams of the buffer fluid. Other undesired particles included in the biological fluid sample can be captured in second streams of the biological fluid sample that generally flow in a straight trajectory through the DLD or nanoDLD arrays. For example, in implementations in which the target particles include exosomes, the undesired particles removed by the separation unit can include potentially contaminating small molecules such as salts, proteins, lipids and the like. The second or innermost checked line (provided adjacent to outlet bus 208), can further include a plurality of openings through which the first streams can exit the DLD or nanoDLD array (e.g., the dark grey region of the separation unit 206) and enter into outlet bus 208 (e.g., in the direction shown by the dashed arrows). The second checked line can also include a plurality of outlet vias through which the respective second streams can be collected and expelled from the microfluidic chip 106 (e.g., as waste fluid).

The outlet bus 208 comprises an etched channel formed within the thickness of the microfluidic chip 106. The outlet bus 208 can receive the filtered stream of the buffer fluid including the target particles from the separation unit 206 and transport the filtered target particle stream to the downstream, sensing element 108 (e.g., in the direction shown by the dashed arrows. In one or more embodiments, the interface (or interfaces) between the outlet bus 208 and the sensing element 108 can include one or more openings (not shown) through which the target particle buffer stream can enter and flow onto and over the sensing element (e.g., in the direction shown by the dashed grey arrows). The sensing element 108 can further include a global outlet via 210 through which the buffer stream can exit the microfluidic chip 106, along with any unreacted and/or unbound particles included in the filtered, target particle buffer stream. In various embodiments, the outlet bus 208 and the inlet bus 204 bus can be etched deeper than both the separation unit 206 and the sensing element 108. The purpose for this is to ensure that fluidic resistance is dropped or decreased across the separation unit 206 and the sensing element 108.

The microfluidic chip 106 also include one or more third inlet vias 212 that are fluidically coupled to the sensing element 108. In the embodiment shown, four third inlet vias 212 are shown, however the number of third inlet vias 212 can vary. The one or more third inlet vias 212 can facilitate introducing a detection fluid onto the sensing element 108 for coating and functionalizing the sensing element 108. For example, the detection fluid can include one or more types of detection molecules or macromolecules (e.g., antibodies, aptamers, etc.), known to chemically react with one or more biomarkers of interest that may be present on or within the separated particles of interest. In some implementations, prior to injecting the biological sample fluid into the microfluidic chip, the detection fluid can be injected through the one or more third inlet vias 212 and flowed onto the sensing element 108 to coat and functionalize the sensing element 108. Excess detection fluid or otherwise portions of the detection fluid that do not coat the surface of the sensing element 108 can also flow through the global outlet via 210.

In the embodiment shown, a circular, distribution bus 214 can be formed around the perimeter of the sensing element 108 (depicted by the thin grey line formed around the sensing element 108) to facilitate evenly distributing the detection fluid and the biological fluid over the surface of the sensing element 108. For example, the distribution bus 214 can be formed around the perimeter of the sensing element 108 and minimize fluidic resistance to induce uniform fluid flow from the perimeter injection sites to the center of the sensing element 108, thereby enabling uniform coverage of coating chemistry and sample over the sensing element during device operation.

In various embodiments, the sensing element 108, the portion of the outlet bus 208 that connects to the sensing element 108, the global outlet via 210, the one or more third inlet vias 212, and the distribution bus 214, can constitute the detection unit of the subject microfluidic chips (e.g., microfluidic chip 106).

Figure 2C:
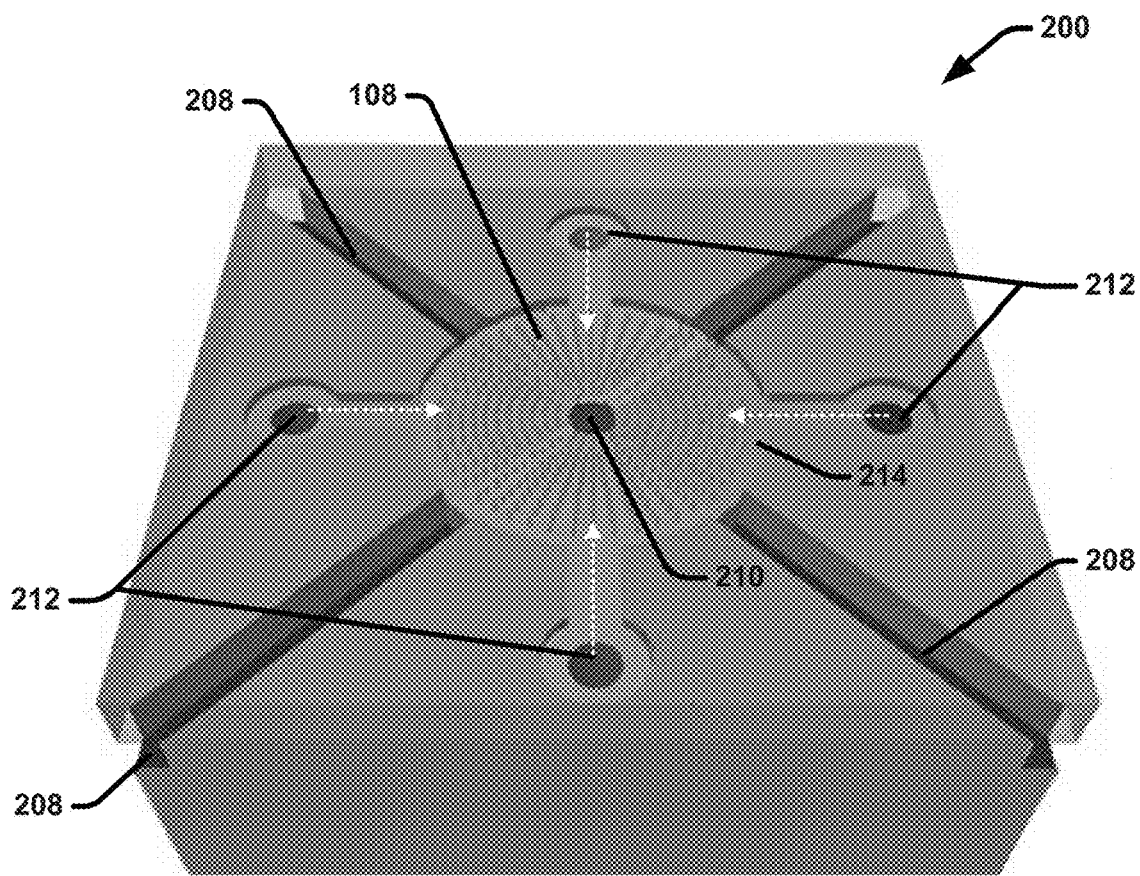
FIGS. 2C-2D present a 3D perspective view of an example detection unit of a microfluidic chip that integrates on-chip particle purification and biomarker detection functionality in accordance with one or more embodiments described herein.
Figure 2D:
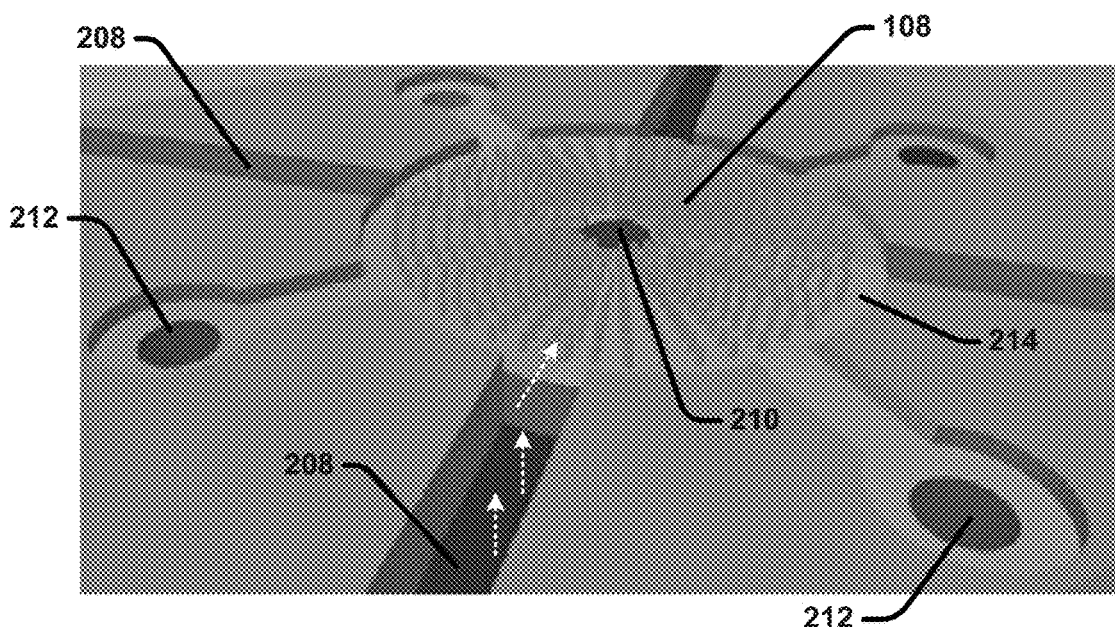

In this regard, FIGS. 2C and 2D present a 3D, perspective view of an example detection unit 200 of a microfluidic chip (e.g., microfluidic chip 106) that integrates on-chip particle purification and biomarker detection functionality in accordance with one or more embodiments described herein. Repetitive description of like elements employed in respective embodiments is omitted for sake of brevity.

As shown in FIG. 2C with respect to the dashed arrow lines, detection fluid can be introduced at the respective third inlet vias 212 and flowed over the sensing element 108 and out the global outlet via 210 to coat and/or functionalize the surface of the sensing element 108. As shown in FIGS. 2C and 2D, the outlet bus 208 can comprise a plurality of deeply etched channels that connect to the sensing element 108. As shown in FIG. 2D with reference to the dashed arrow lines, after the sensing element has been functionalized, a stream of buffer fluid comprising purified target particles can flow from the separation unit 206, up through the outlet bus 208 channels and onto the sensing element 108. Excess detection fluid and target particle buffer stream can further flow into the global outlet bus 210 to be removed from the microfluidic chip 106.

With reference again to FIGS. 1A and 1B in connection with reference to FIGS. 2A-2D, in various embodiments, the microfluidic bussing network (e.g., including the global inlet via 202, the inlet bus 204, the second inlet vias (not shown) for introducing the buffer fluid into the separation unit 206, the plurality of outlet vias (not shown) for removing waste fluid from the separation unit 206, the outlet bus 208, the global outlet via 210, and/or the one or more third inlet vias 212) can be fluidically coupled to one or more fluid inlets and outlets provided within the bottom plate 102B of the housing 102 via which the microfluidic chip receives and excretes fluids. For example, in one or more embodiments, the housing 102 can be or include a flow cell or another form of packaging that facilitates flowing or otherwise injecting fluid into one or more input vias connected to the bussing network of the microfluidic chip 106 and removing fluid from the microfluidic chip 106. The housing 102 can be formed with various materials, including silicon, glass, plastic, or a combination thereof. In this regard, the bottom plate 102B of the housing 102 can include one or more inlet ports through which fluid is injected (e.g., using a syringe, pipette, or the like) into one or more flow cell channels (not shown) and/or reservoirs (not shown) provided on or within the bottom plate 102B. The one or more flow cell channels/ and reservoirs can be fluidically coupled to the microfluidic bussing network of the microfluidic chip 106. The bottom plate 102B can further include one or more output ports through which fluid is exported or otherwise removed from the microfluidic chip 106 and/or one or more reservoirs of the housing 102. In this regard, one or more fluids can flow into the bottom plate 102B of separation-purification apparatus 100, through the microfluidic chip 106, and then out of the microfluidic chip via the housing 102.

For example, FIG. 3A presents a 3D view of the bottom plate 102B of the housing 102 as separated from the microfluidic chip 106 and the top plate 102A. Repetitive description of like elements employed in respective embodiments is omitted for sake of brevity.

With reference to FIG. 3A, in conjunction with reference to FIGS. 1A-1B and 2A-2D, in the embodiments shown, the bottom plate 102B of the housing can include a chip pocket 312 that can receive the microfluidic chip 106. In this regard, the microfluidic chip 106 can be inserted into the chip pocket 312 such that a bottom surface (e.g., the surface opposite the sensing element 108), is opposed to the upper surface of the bottom plate 102B. The bottom surface of the microfluidic chip 106 can further include openings or vias which can correspond to one or more inlet vias and outlet vias of the microfluidic chip (e.g., the global inlet via 202, the global outlet via 210, and other vias described below). In some embodiments, these openings or vias in/through the bottom surface of the microfluid chip can align with and fluidically couple to corresponding fluid inlets/outlets provided by the bottom plate 102B of the housing.

The bottom plate 102B includes three inlet ports or capillaries, including inlet port 112, inlet port 114 and inlet port 116. These inlet ports can respectively be used to inject fluid (e.g., the biological fluid sample, the buffer fluid, and the detection fluid), into the microfluidic chip. The bottom plate 102B also includes two outlet ports, outlet port 118 and outlet port 120. These outlet ports can respectively be used to remove fluid (e.g., waste fluid, excesses detection fluid, and purified sample fluid as it flows over the sensing element 108 and out through the global outlet via 210), from the microfluidic chip 106 and the bottom plate 102B. In some embodiments, a single outlet port can be used. In other embodiments, more than two output ports can be used. In the embodiment shown, the inlet ports and outlet ports are depicted as tubes that extend from sides of the bottom plate 102B. However, it should be appreciated that the location of the respective inlet and outlet ports can vary. In addition, although the inlet ports are shown as tubes, it should be appreciated that these tubes connect to corresponding openings/microfluidic channels (not shown) formed within the body of the bottom plate. In this regard, the tubes can be removably attached/detached from corresponding openings/microfluidic channels in the bottom plate 102B.

For example, in various embodiments, an upper surface region of the bottom plate 102B can include a plurality of fluidic connections and fluid reservoirs which can receive fluid from the one or more inlet ports (e.g., inlet port 112, inlet port 114 and/or inlet port 114) for introducing into the microfluid chip, and/or receive fluid as it is excreted from the microfluid chip. For example, in the embodiment shown, these fluidic connections/reservoirs respectively include fluidic connection 302', buffer fluid reservoir 304, waste fluid reservoir 306, detection fluid reservoir 308, and fluidic connection 310'. The respective reservoirs, including the buffer fluid reservoir 304, the waste fluid reservoir 306, and the detection fluid reservoir 308, can be fluidic pools that can contain a fluid within. Specifically, in one or more embodiments, the buffer fluid reservoir 304 can receive and contain buffer fluid for injection into the separation unit of the microfluidic chip, the waste fluid reservoir 306 can receive and contain waste fluid (comprising unwanted particles) removed by the separation unit, and the detection fluid reservoir 308 can receive and contain detection fluid comprising the surface chemistry molecules/macromolecules for coating the sensing element 108. Each of these reservoirs can include one or more openings (not shown) through which the corresponding fluid can be injected into the reservoir and one or more openings (not shown) through which fluid can removed from the reservoir.

In the embodiment shown, the buffer fluid reservoir 304, waste fluid reservoir 306, detection fluid reservoir 308, are formed on/within an upper surface region of the bottom plate 102B. For example, in some implementations, the respective reservoirs can be exposed on the top surface of the bottom plate on the housing. With these embodiments, the reservoirs can become enclosed by the bottom surface of the microfluidic chip when the microfluidic chip is inserted into the chip pocket 312. In this regard, when the microfluidic chip is inserted into the chip pocket, the bottom surface of the microfluidic chip can cover and enclose the reservoirs. In other implementations, a top surface of the bottom plate 102B can enclose the reservoirs. In another embodiment, one or more of these reservoirs can be formed within the microchip 106 and/or an intermediary layer (not shown) between the microchip 106 and the bottom plate 102B. In various embodiments, these three reservoirs are collectively referred to herein as the reservoir region.

In one or more embodiments, fluidic connection 302' can correspond to an opening in an upper surface of the bottom plate 102B that can align with and connect to the global inlet via 202 of the microfluid chip. In accordance with this example embodiment, the inlet port 112 can connect to the fluidic connection 302' and the global inlet via 202 of the microfluidic chip 106 when the microfluid chip 106 is inserted into the chip pocket 102. In this regard, inlet port 112 can be configured to receive a biological fluid sample and facilitate flowing the biological fluid sample through a channel (not shown) formed within the bottom plate 102B that connects to the fluidic connection 302' and which is further aligned with and connects to the global inlet via 202 of the microfluidic chip 106. In one or more embodiments, the interface between the fluidic connection 302' and the global inlet via 202 can employ an o-ring seal or gasket to maintain fluidic isolation between the reservoirs (via compressive pressure applied to the o-ring seal or gasket) and controlling passage of the biological fluid from the bottom plate 102B, through global inlet via 202 and into the inlet bus 204. The inlet bus 204 can further receive the biological fluid and pass the fluid through the microfluidic chip 106 for processing by the separation unit and the detection unit of the microfluidic chip 106, as herein. In some implementations, the biological fluid sample can be injected into the inlet port 112 via a pipette, via a syringe, or via from another off-chip biological sample reservoir connected to the inlet port 112 via a suitable tube or capillary. In various embodiments, the biological fluid sample can be injected through the inlet port 112 and into the microfluidic chip 106 (e.g., via the first global inlet via) using a pressure driving system or device (not shown) that is external to the separation-purification apparatus 100.

Similarly, in some embodiments, the fluidic connection 310' can correspond to an opening in an upper surface of the bottom plate 102B that can align with and connect to the global outlet via 210 of the microfluid chip. In accordance with this example embodiment, the outlet port 120, can be fluidically connected to the fluidic connection 310' via a microfluidic channel (not shown) formed within the bottom plate 102B (and through the center of the detection fluid reservoir 308). The fluidic connection 310' can further be fluidically connected to the global outlet via 210 of the microfluidic chip 106 when inserted into the chip pocket 312. In this regard, the outlet port 120 can be configured to export fluid passed over the sensing element 108 and flowed into the global outlet via 120. For example, in some implementations, this fluid can initially include excess detection fluid that flows from inlet port 116 through separation-purification apparatus 100, over the sensing element 108 of the microfluidic chip 106 and exits the separation-purification apparatus 100 via outlet port 120. In this regard, outlet port 120 can provide for removing excesses reagent chemistry (e.g., antibodies, aptamers, etc.) from the sensing element 108 in association with the coating process used to functionalize the sensing element 108. Outlet port 120 can also be employed to remove the stream of buffer fluid including separated particles of interest as the stream is passed over the sensing element 108 to detect presence of biomarkers on or within the particles of interest. In this regard, a stream of buffer fluid including separated particles of interest can flow from the separation unit 206 of the microfluidic chip 106 to the downstream detection unit and over the sensing element 108 in a steady manner, allowing for biomarkers to contact and react with the sensing element 108, while unreacted or unbound particles in the buffer stream are excreted through the outlet port 120. In some implementations, exit of fluid through the global outlet via 210 can be contained via an o-ring or another suitable gasket formed around and//or within the global outlet via 210 and/or the fluidic connection 310'.

The introduction of buffer fluid and detection fluid into the microfluidic chip 106 via the corresponding buffer fluid reservoir 304 and detection fluid reservoir 308 (when the microfluidic chip is inserted into the chip pocket 312), and the removal of waste fluid from the microfluidic chip 106 via the corresponding waste fluid reservoir 306, is discussed with reference to FIGS. 3B and 3C in connection with FIGS. 1A-1B, 2A-2D and 3A.

Figure 3B:
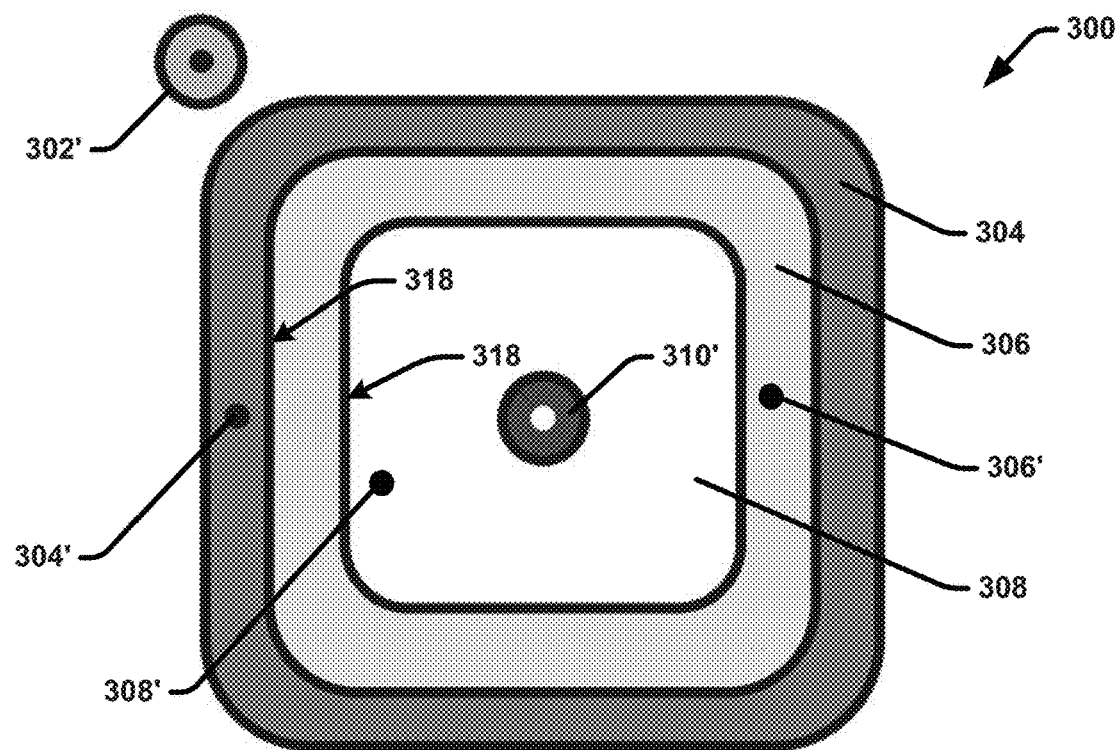
FIGS. 3B and 3C present orthogonal, top-down views of an example reservoir region that couples with a microfluidic chip to facilitate on-chip particle purification and biomarker detection functionality in accordance with one or more embodiments described herein.
Figure 3C:
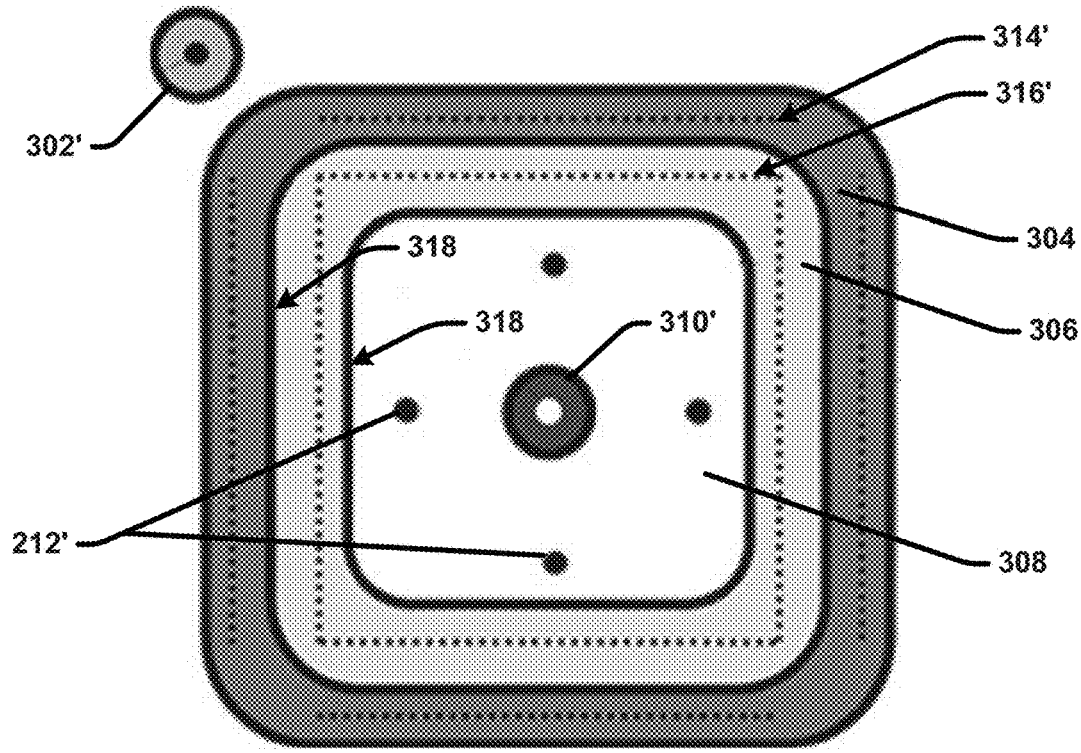

In this regard, FIGS. 3B and 3C present orthogonal, 2D, top-down views of an example reservoir region that couples with a microfluidic chip to facilitate on-chip particle purification and biomarker detection functionality in accordance with one or more embodiments described herein. The reservoir region can comprise three reservoirs including the buffer fluid reservoir 304, waste fluid reservoir 306, and detection fluid reservoir 308. Each of the reservoirs can be enclosed fluidic pools that can contain a fluid within. In this regard, each of these fluid reservoirs can be defined by an upper surface, a bottom surface, and a fluidic space between the bottom surface and the upper surface. FIG. 3B depicts the bottom surface 300 of the reservoir region. FIG. 3C depicts the upper surface 301 of the reservoir region. In the embodiment shown in FIG. 3A, the reservoir region is formed within an upper portion of the bottom plate 102B. However, the specific location of the respective reservoirs can vary so long as they are located between the active features of the microfluidic chip (e.g., the separation unit and the detection unit) and the corresponding fluidic inlets/outlets of the bottom plate 102B. In this regard, in some embodiments, the bottom surface of the 300 of the reservoir region can be part defined within the bottom plate 102B and the upper surface 300 of the reservoir region can also be defined by/within the bottom plate (e.g., the upper surface of the bottom plate 102B). In other embodiments, the upper surface 301 of the reservoir region can be defined by the bottom surface of the microfluidic chip 106. For example, the reservoirs can be exposed and formed on the top surface of the bottom plate 102B. The exposed reservoirs can further become enclosed and covered when the microfluidic chip 106 is inserted into the chip pocket 312. With this implementation, the bottom surface of the microfluidic chip can correspond to the top surface 301 of the reservoir region. Other configurations are envisioned.

Each of these reservoirs (e.g., the buffer fluid reservoir 304, the waste fluid reservoir 306, and the detection fluid reservoir 308) can include one or more openings through which the corresponding fluid can injected into the reservoir and one or more openings through which fluid is removed from the reservoir. For example, as shown in FIG. 3B, each of the reservoir regions can include a single fluidic connection or opening through which fluid is injected from the bottom plate 102B and into the reservoir, or from which fluid is removed from the reservoir and ejected through the bottom plate 102B. In particular, the buffer fluid reservoir 304 can include fluidic connection 304' through which buffer fluid can be injected into the buffer fluid reservoir 304. Waste fluid reservoir 306 can include fluidic connection 306' through which waste fluid can be extracted from the waste fluid reservoir 306. Detection fluid reservoir 308 can include fluidic connection 308' through which detection fluid can be inserted into the detection fluid reservoir 308. For example, with reference to FIGS. 3A and 3B, in some embodiments, inlet port 114 can be configured to receive and facilitate injection of the buffer fluid into the buffer fluid reservoir 304 via a microfluidic channel (not shown) formed within the bottom plate 102B that connects the inlet port 114 to the microfluidic connection 304'. In some implementations, an o-ring or another suitable gasket material can form a fluid seal at the interface of the fluidic connection 304' and the fluidic inlet connected thereto. Similarly, inlet port 116 can be configured to receive and facilitate injection of the detection fluid into the detection fluid reservoir 308 via a microfluidic channel (not shown) formed within the bottom plate 102B that connects the inlet port 116 to the microfluidic connection 308'. In some embodiments, the solid lines 318 that separate the reservoirs can be or correspond to o-rings. With these embodiments the o-rings do not seal the fluid at the interface of the fluidic connections 308' and 304'. Rather, they corral the fluid within the respective reservoirs. In addition, the outlet port 118 can be configured to receive and facilitate removal of waste fluid that is collected in the waste fluid reservoir 306 (e.g., as injected from the separation unit of the microfluidic chip into the waste fluid reservoir 306) via a microfluidic channel (not shown) formed within the bottom plate 102B that connects the oulet port 118 to the microfluidic connection 306'. In some implementations, an o-ring or another suitable gasket material can form a fluid seal at the interface of the fluidic connection 308' and the fluidic inlet connected thereto.

With reference to FIG. 3C in connection with reference to FIG. 2B, in one or more embodiments, the upper surface of the buffer fluid reservoir 304 can align with and be fluidically connected to the plurality of input vias of the separation unit of the microfluidic chip 106. For example, the respective dashes of the dashed line 314' depicted within the buffer fluid reservoir 304 can respectively correspond projected inlet via locations of the separation unit through which the buffer fluid included in the buffer fluid reservoir 304 can be pushed to enter through aligned input vias (e.g., the second input vias described above) of the separation unit. With these implementations, the buffer fluid, can be injected into the buffer fluid reservoir 304 of the housing 102 via inlet port 114 and fluidic connection 304'. As the buffer fluid reservoir 304 fills with buffer fluid, the buffer fluid can be pressure driven through the aligned and fluidically connected second inlet vias of the separation unit 206. For example, in some embodiments, a pressure driving device or system coupled to the separation-purification apparatus 100 can be used to pressure drive the second fluid or buffer fluid through the inlet port 114 and/or fluid the buffer fluid reservoir 304 and onto the microfluidic chip 106. In other implementations, the second fluid can be injected into inlet port 114 via a pipette, a syringe, or another suitable injection means. Similarly, the upper surface of the waste fluid reservoir 306 can align with and be fluidically connected to the plurality of outlet vias of the separation unit of the microfluidic chip 106 through which waste fluid is excreted. In this regard, the respective dashes of the dashed line 316' depicted within the waste fluid reservoir 306 can respectively correspond to projected outlet via locations of the separation unit through which waste fluid can be ejected into the waste fluid reservoir 106. In addition, a plurality of fluidic connections 212' can be included in the upper surface of the detection fluid reservoir 308 which can be fluidically connected to the one or more third inlet vias 212. With these implementations, the detection fluid reservoir 308 can be fluidically coupled with the one or more third inlet vias 212 of the microfluidic chip 106 through which the detection fluid can be injected and flowed onto the sensing element 108 to facilitate coating the sensing 108 prior to flow of biological sample fluid through the microfluidic chip 106. In this regard, as the detection fluid is injected through inlet port 116 and fills the detection fluid reservoir 308 via fluidic connection 308', the detection fluid can evenly enter the one or more third inlet vias 212 and evenly coat the sensing element 108. For example, in some embodiments, the pressure driving device or system coupled to the separation-purification apparatus 100 can also be used to pressure drive the detection fluid through inlet port 116 and/or the additional fluid reservoir and onto the microfluidic chip 106. In other implementations, the third fluid can be injected into inlet port 116 via a pipette, a syringe, or another suitable injection means.

With reference again to FIGS. 1A and 1B, the separation-purification apparatus 100 can further include a sealing layer 104 formed between the microfluidic chip 106 and the housing 102. For example, in the embodiment shown, the sealing layer 104 is provided between an upper surface of the bottom plate 102B and a bottom surface or backside of the microfluidic chip 106. In other implementations, the sealing layer 104 can be formed at an interface between the reservoir region and the upper surface of the bottom plate 102B. In yet another embodiment, the sealing layer 104 can be formed at an interface between the reservoir region and the bottom surface of the microfluidic chip.

The sealing layer 104 can comprise one or more materials that facilitate creating a fluidic seal between one or more vias or openings in the backside of the microfluidic chip 106, and one or more ports, capillaries, channels, and/or reservoirs of the bottom plate 102B and/or the reservoir region. For example, in some implementations, the sealing layer 104 can comprise a gasketing material that creates a fluidic seal at the interface between one or more openings or vias on the backside of the microfluidic chip 106, and one or more adjacent/aligned openings (e.g., a capillary, a channel, a via, a reservoir, etc.) in the upper surface of the bottom plate 102B. For example, in some embodiments, the gasket material can be constructed from o-rings or a polymer, such as an elastomer, a thermoset, a thermoplast, and the like. In some implementations, the gasket material can be formed by 3D printing, stamped, embossed, injection molded, laser cut, or ablated from the polymeric starting material. For example, as can be observed by comparing FIGS. 2B and 3B, the placement of the global and local via inlet and outlets on the chip surface are superimposed or projected onto common reservoirs, whose borders can be defined by sets of o-rings on the backside of the chip, one means of providing a fluidic seal at the interface between the chip and flow-cell/packing.

The sealing layer 104 can thus comprise one or more or more o-rings or gasket arrangement that ensure each reservoir of the housing and/or microfluidic chip is continuous, allowing one fluid type to be universally introduced or extracted from one associated via or set of vias on the microfluidic chip 106. In this regard, although the sealing layer 104 is depicted a continuous layer of material, it should be appreciated that this depiction is merely for exemplary purposes. For example, in implementations, the sealing layer 104 can consist of a plurality of o-rings formed in an arrangement only between portions of the interface between the microfluidic chip 106 and the housing 102 where adjacent openings are located. This arrangement allows the simultaneous fluid loading of all vias associated with a particular fluid group. Importantly, the fluid to/from each reservoir in the gasket must have an inlet port or outlet port (e.g., one or more of ports 112-120) that can be accessed from the housing 102. In the embodiment shown, only one access port to each reservoir is used to minimize the design complexity of the housing 102.

Figure 4:
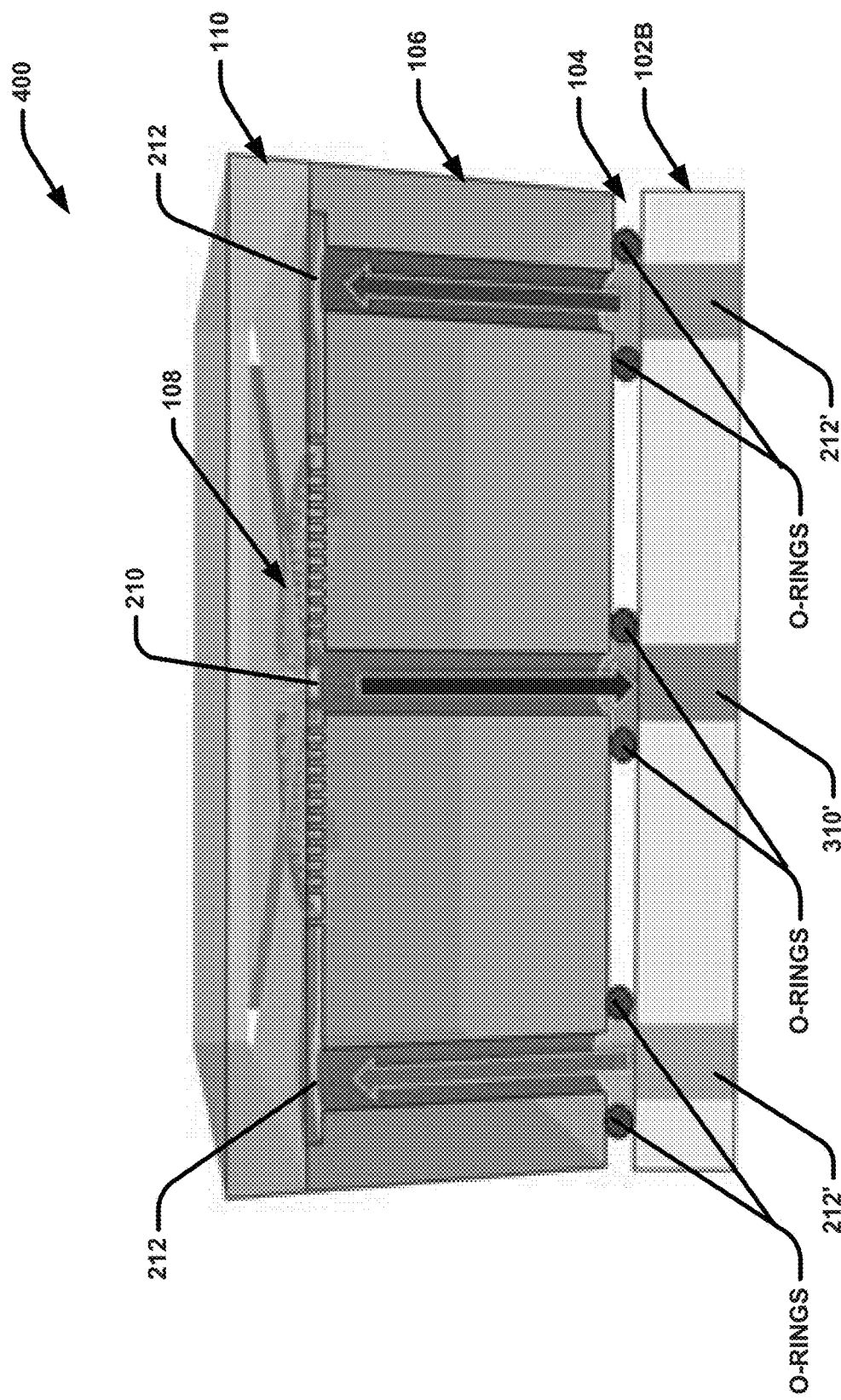
FIG. 4 illustrates a cross-sectional view of an example detection unit region of a non-limiting separation-purification apparatus that integrates on-chip particle purification and biomarker detection functionality in accordance with one or more embodiments described herein.

FIG. 4 illustrates an example cross-sectional view the detection region 400 of separation-purification apparatus 100 taken along axis A-A' shown in FIG. 1 in accordance with one or more embodiments described herein. Repetitive description of like elements employed in respective embodiments is omitted for sake of brevity.

With reference to FIG. 4 in conjunction with FIGS. 1, 2A-2D and 3A-3C, in the embodiment shown, three vias or channels are formed within the thickness of the substrate (e.g., silicon) of the microfluidic chip 106, respectively corresponding two of the third inlet vias 212, and the global outlet via 210. In this regard, the inlet vias 212 respectively connect to and/or correspond to respective third inlet vias 212 through which detection fluid can be introduced onto the sensing element 108. Likewise, outlet via 210 connects to and/or corresponds to outlet via 210 through which excess detection fluid and biological fluid sample can be removed from the microfluidic chip. These channels are respectively fluidically coupled to and aligned with corresponding fluidic connections 212' and 310' in the reservoir layer. For example, inlet vias 212 are respectively connected to fluidic connections 212' in the detection fluid reservoir 308, and outlet via 210 is connected to the fluidic connection 310' which connects to the outlet port 120. In accordance with this embodiment, the sealing layer 104 consists or o-rings respectively formed between the bottom surface of the microfluidic chip 106 and the upper surface of the reservoir layer (e.g., included in the bottom plate 102B) around the aligned channels vias 212 and 210 and their corresponding fluidic connections in the reservoir layer.

With reference again to FIG. 1, in various embodiments, although not shown, separation-purification apparatus 100 can be coupled to a pressure-driving system to control flow of the various fluids (e.g., the biological sample fluid, the buffer fluid, the detection fluid, and other potential cleaning/preparation fluids) into, out of, and through the housing 102 and the microfluidic chip 106. The pressure-driving system can be a fully automated pressure driving machine, a manually operated pressure driving machine, or a combination thereof. The pressure driving system can form a pressure seal between the inlet ports (e.g., inlet port 112, inlet port 114, and inlet port 116) and the respective reservoirs, channels, inlets, etc., of the housing 102, and/or the respective outlet ports (e.g., outlet port 118 and outlet port 120). In this regard, the pressure driving system can apply pressure to initiate fluid flow of one or more fluids within the different fluid reservoirs located within the housing and a reservoir comprising the biological sample fluid, referred to herein as the sample fluid reservoir. Although not explicitly shown in FIG. 3B, in some implementations, the housing 102 can include the sample fluid reservoir formed therein in which the biological sample fluid can be pre-loaded prior to running through the microfluidic chip 106. In other implementations, the sample fluid reservoir can be provided external to separation-purification apparatus 100. The sample fluid reservoir can be fluidically coupled to the global inlet via 202 by way of the (gasketed) opening 302 of the housing 102 aligned therewith.

The separation-purification apparatus 100 can further include a capping layer 110 formed on or over the microfluidic chip 106. In various embodiments, the capping layer 110 can include a transparent or semi-transparent material (e.g., glass, plastic, etc.) that provides for hermetically sealing one or more fluidic elements (e.g., busses, channels, vias, reservoirs, sensing element 108 chambers, etc.), provided on or within the microfluidic chip 106. In addition, by employing a transparent capping layer 110, the upper surface of the microfluidic chip including the sensing element 108 can be visually observed (e.g., via the naked eye, a microscope, or another suitable imaging device).

In some embodiments, the microfluidic chip 106 can be permanently sealed within the housing 102. With these embodiments, formation of separation-purification apparatus 100 can include a bonding procedure wherein the backside of the microfluidic chip 106 is bonded to or otherwise affixed to the upper surface of the bottom plate 102B of the housing. The capping layer 110 can further be bound to the microfluidic chip 106 and/or the housing 102 to permanently seal the microfluidic chip 106 within the housing 102. In other embodiments, the microfluidic chip 106 can be removably attached to the housing 102. With these embodiments, the housing 102 can be re-used with new microfluidic chips inserted therein (or cleaned microfluidic chips reinserted therein). For example, in one implementation, the housing 102 can be configured to receive and snap-in, screw in, lock-in, etc., the microfluidic chip 106 in a manner that allows for the chip to be easily removed after use. The capping layer 110 can further be configured to removably attach or open and close to cover and seal the microfluidic chip 106 within the housing 102 during use. Alternatively, the capping layer 110 can be permanently affixed to the surface or the microfluidic chip 106. With this implementation, the microfluidic chip 106 with the capping layer 110 bound thereto can for a single unit that can be inserted into the housing 102. With these implementations, the top plate 102A of the housing can be attached to the bottom plate 102B of the housing (e.g., via one or more screws or another mechanism) to sandwich and seal the microfluidic chip 106/capping layer 110 unit therein.

In accordance with an example usage scenario in which separation-purification apparatus 100 is used for biomarker discover and/or liquid biopsy screening, separation-purification apparatus 100 can be operated as follows. Optionally, the microfluidic chip 106 can be pre-wet with antifouling chemical agents including, but not limited to buffers of varying pH and ionic strength levels, surfactants, and biological coating agents such as bovine serum albumin (BSA). Next, a sample (including urine, blood, plasma, saliva, cell culture media, etc.), buffer, and antibody or aptamer containing chemistries can be loaded (e.g., via pipetting or another suitable mechanism) into separate reservoirs of the housing 102 (e.g., located on or within the bottom plate 102B) with the microfluidic chip 106 sealed inside. The housing can further be being placed into or otherwise coupled to a pressure driven system to initiate purification and detection. Initially, the pressure-driven system can apply pressure to force the flow of the antibody or aptamer containing fluid onto the sensing element 108 to surface functionalize the sensing element 108. The pressure-driven system can then stop the flow of antibody or aptamer chemistry and initiate the flow of sample and buffer simultaneously to initiate purification and downstream immunocapture of target macromolecules that flow over the sensing element 108. The presence of one or more exosomes or other biomarkers bound to the antibodies or aptamers coated on the surface of the sensing element 108 can be observed either directly by an operator (e.g., via the naked eye, through a microscope lens placed over the sensing element 108, etc.) or computer-based reception and analysis of image data captured of the sensing element 108.

Figure 5:
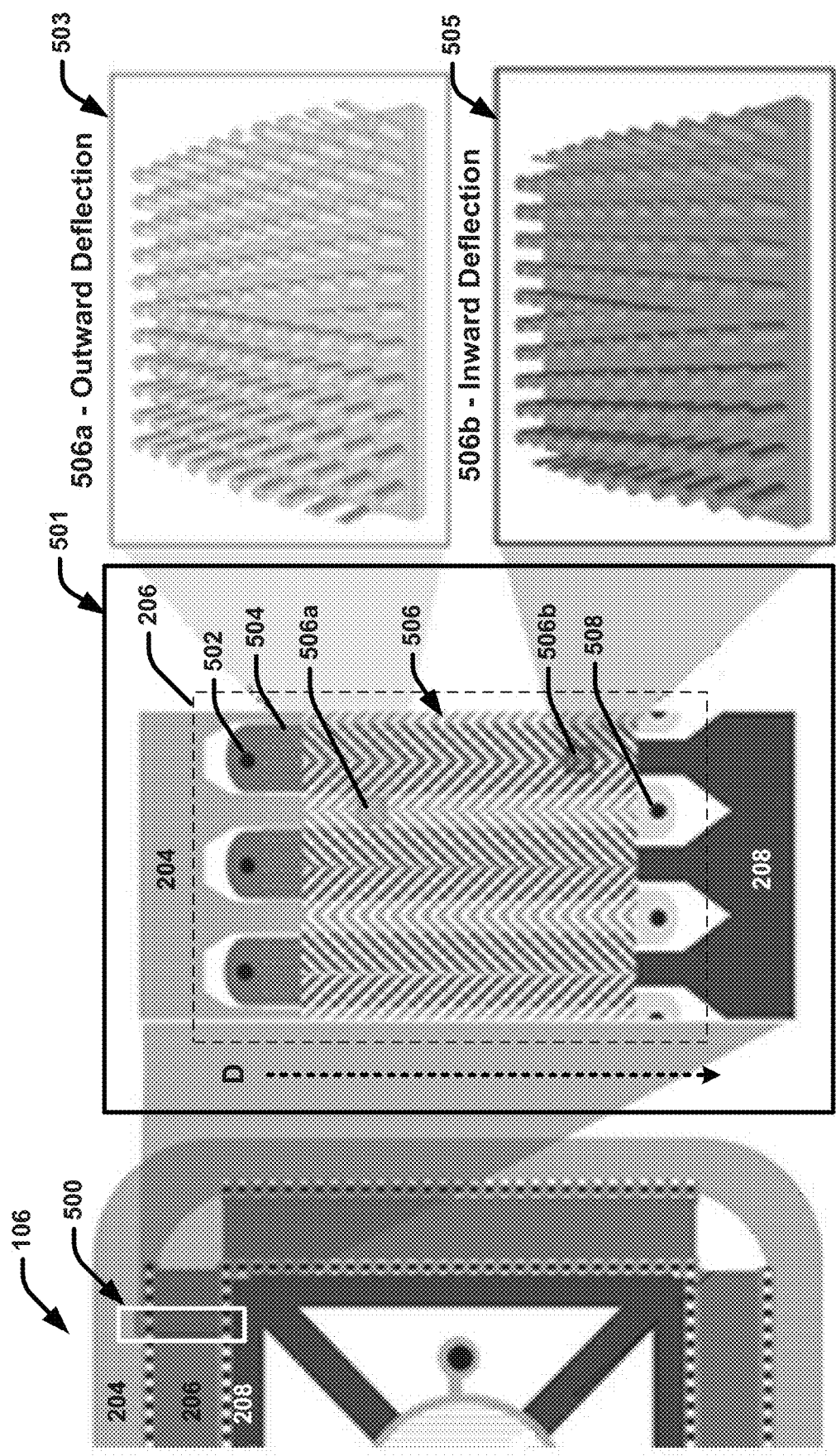
FIG. 5 illustrates an enlarged view of an example separation unit of an example microfluidic chip that integrates on-chip particle purification and biomarker detection functionality in accordance with one or more embodiments described herein.

FIG. 5 illustrates an enlarged view of an example separation unit 206 of the microfluidic chip 106 in accordance with one or more embodiments described herein. For example, call-out box 501 presents and enlarged or zoomed-in view of the area of the microfluidic chip 106 encircled by box 500. Repetitive description of like elements employed in respective embodiments is omitted for sake of brevity.

With reference to call-out box 501, the separation unit 206 can comprise a plurality of DLD on nanoDLD arrays formed between inlet bus 204 and outlet bus 208. In this regard, the size and spacing of the respective pillars used for DLD array can be adapted to a particular target particle size or size range, which can include nanoparticles, such as exomes, viruses, DNA sequences, RNA sequences, etc., as well as larger particles such as cells. Thus, in implementations in which the microfluidic chip 106 is used for exosome filtration and biomarker analysis, the separation unit 206 can employ nanoDLD arrays. For larger particles, the separation unit 206 can employ DLD arrays with pillars and/or pillar spacing adapted to filter particles greater than 999 nm. For ease of explanation, the DLD array portion of the separation unit 206 is referred to as a nanoDLD array 506.

The separation unit 206 can employ a multiplexed arrangement of a plurality of conjoined nanoDLD array pillars or units to facilitate enhanced throughput of target particle isolation from sample biological fluid. For example, with reference to FIG. 2B and FIG. 5, the separation unit 206 can employ four rows of densely packed nanoDLD array pairs arranged inside of the circular, inlet bus 204 feed that distributes the sample fluid from the global inlet via 202. For example, the number of nanoDLD array pairs that can be integrated into the microfluidic chip can range from the thousands to the hundreds of thousands depending on the size of the chip. Usage of this massive, multiplexed parallelization framework can substantially increase the throughput rate of the separation unit 206 (e.g., to around 1.0 mL of sample fluid per hour or greater).

The nanoDLD array 506 can include alternating pillar array units with different pillar angles for outward deflection of an incoming sample fluid, and inward deflection for incoming buffer fluid. For example, in the embodiment shown, the separation unit 206 can include a plurality of second inlet vias 502 through which buffer fluid can be introduced into the separation unit 206 and flowed downstream (e.g., in the direction of arrow D) in association with simultaneous flow of biological sample fluid through the separation unit 206 from inlet bus 204 (e.g., in the direction of arrow D). As described with reference to FIGS. 2B and 3C, for example, the second inlet vias 502 can correspond to the respective dark boxes of the first checkered line drawn at the interface between the inlet bus 204 and the dark grey region of the separation unit 206. The second inlet vias 502 can further connect to the buffer fluid reservoir 304.

A zoomed-in view of the nanoDLD array pairs is shown in call out-boxes 503 and 505. As shown in call-out box 501 and call-out box 503, the nanoDLD array 506 can include outward deflection units 506a positioned adjacent to the entry region of the separation unit 206 with the biological fluid sample is passed from the inlet bus 204. As shown in call-out box 501 and call-out box 505, the nanoDLD array 506 can further include inward deflection units 506b positioned adjacent to the second inlet vias 502 through which the buffer fluid is injected. As a result, larger, target particles of interest included in the biological fluid sample can be directed in an inward flow path direction that causes a first stream of buffer fluid including the particles of interest to flow toward and into the outlet bus 208 where they are collected. Smaller, unwanted particles (e.g., salts, proteins, lipids, and other small biomolecules/macromolecules), collectively referred to herein as waste particles, can be directed in an outward flow path direction that causes a second stream of buffer fluid to flow toward and into a plurality of outlet vias 508. For example, as described with reference to FIGS. 2B and 3C, the outlet vias 508 can correspond to the respective dark boxes of the second checkered line drawn at the interface between the dark grey region of the separation unit 206 and the outlet bus 208. The outlet vias 508 can further align with and connect to the waste fluid reservoir 306. In this regard, the portion of the buffer stream including the waste particles can flow into the waste fluid reservoir 306 via the outlet vias 508 where the waste fluid can be collected and further exported off the chip and the housing 102 (e.g., through outlet port 118).

In the embodiment shown, the separation unit 206 can also include a filtration element 504 (depicted by the plurality of speckles or dots) provided at or near the initial entry points of the buffer fluid and the sample fluid into the separation unit 206. For example, the filtration element 504 can be formed upstream of the nanoDLD array 506. The filtration element 504 can (optionally) be used to filter out or remove certain large particles of size greater than a defined threshold size, such as a size greater than the target particles (e.g., greater than exosomes). In one or more embodiments, the filtration element can include but is not limited to, a cross-flow of serpentine filters, traps, sieves, bladed loading features or a number of other microfluidic filter arrangements to capture cells, larger cellular debris, and/or larger multivesicular bodies (MVBs) while letting desired colloids pass into the downstream, nanoDLD array 506.

Figure 6:
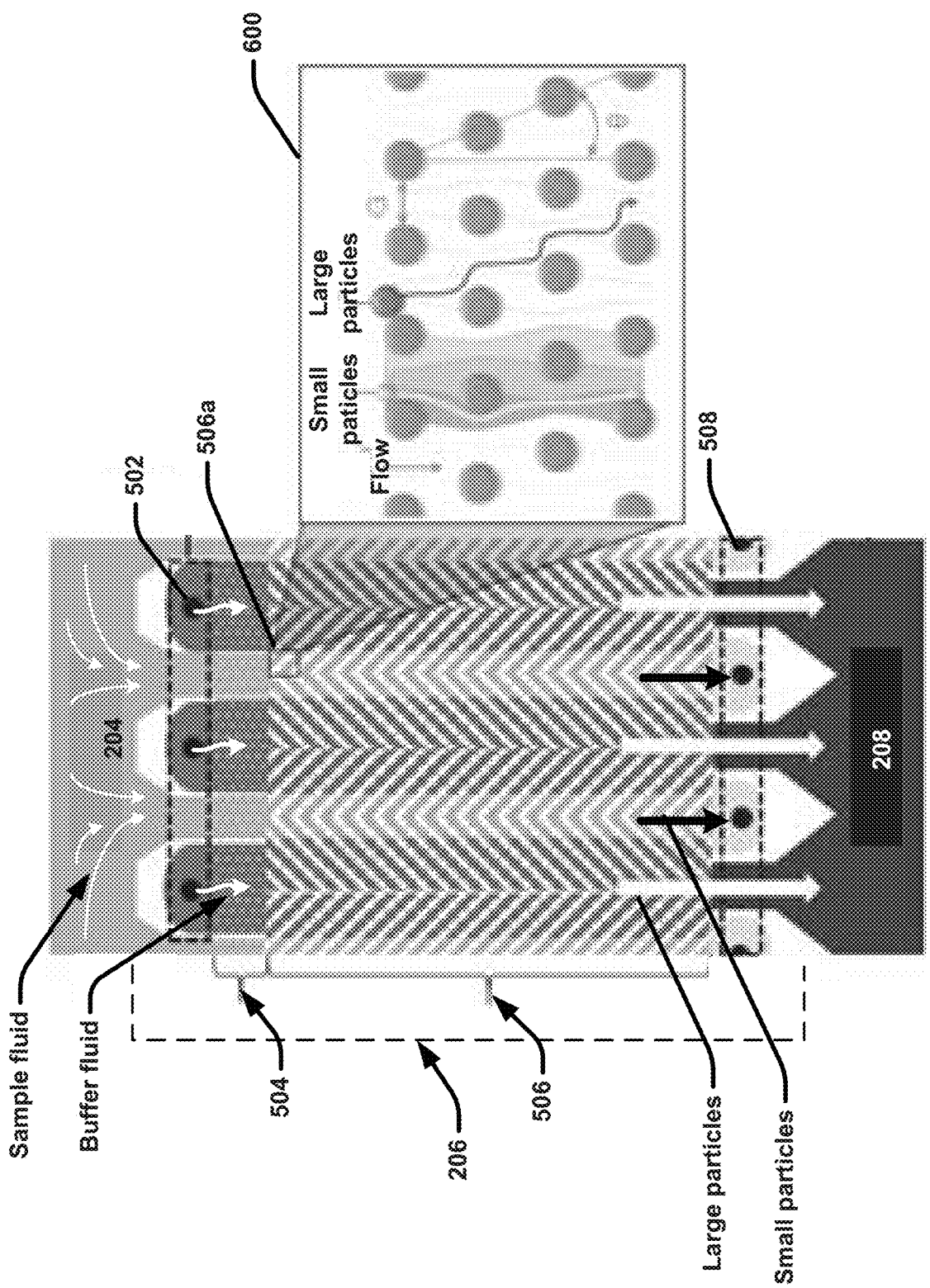
FIG. 6 illustrates another enlarged view of an example separation unit of an example microfluidic chip that integrates on-chip particle purification and biomarker detection functionality in accordance with one or more embodiments described herein.

FIG. 6 illustrates another enlarged view of the portion of the microfluidic chip 106 included in call-out box 401. FIG. 6 further includes call-out box 600 depicting a nano-scale view of one of the outward deflection units 506a in association with simultaneous flow of sample biological fluid and buffer fluid through the nanoDLD arrays in accordance with one or more embodiments described herein. Repetitive description of like elements employed in respective embodiments is omitted for sake of brevity.

FIG. 6 highlights an example process of operation for the separation unit 206 of example separation-purification apparatus 100. In the embodiment shown, the separation process of the separation-purification apparatus 100 involves inlet bus 204 for introduction of sample fluid, second inlet vias 502 through which buffer fluid is injected, filtration element 504, nanoDLD array 506, outlet vias 508 for excreting waste fluid, and outlet bus 208 for collecting purified or extracted particles of interest (e.g., exosomes) and carrying the particles of interest to the downstream detection unit. In this regard, with reference to FIGS. 2B, 3B and FIG. 6, a sample fluid, such as plasma, cultured medium, urine, etc., can be introduced into the microfluidic chip 106 (e.g., at global via 202), and fed through the (circular) inlet bus 204, which in turn, injects the sample through openings at the interface of the inlet bus 204 and the separation unit 206. For example, these openings are located adjacent to the outward deflection units 506a of the nanoDLD array 506. Buffer fluid is further simultaneously injected into the separation unit 206 through the second inlet vias 502 adjacent to the inward deflection areas of the nanoDLD arrays. The buffer fluid can provide a fresh purification medium. Prior to flow of the sample fluid through the nanoDLD array 506, the filtration element 504 can remove larger particles of material from the incoming sample fluid that might otherwise clog at the interface of nanoDLD arrays, reducing longevity.

As shown in FIG. 6, as the fluid sample and the buffer fluid simultaneously flow through the nanoDLD array 506, the large target particles of a defined size range (e.g., exosomes having a defined size range), are deflected or bumped into a portion of the buffer fluid which gets focused at the inward deflection unit/outward deflection unit junction. As a result, the large target particles are directed into the outlet bus 208. Smaller unwanted particles, such as salts, small molecules, lipids, proteins, etc. maintain their general trajectory in the direction of the sample fluid flow toward the outlet vias 508, also referred to herein as the waste outlets. Through this process, a particular purified size range of target particles (e.g., exosomes) can be selectively loaded into the outlet bus 208. This purification process, in effect, acts as a bandpass filter to remove the background contamination below and larger material above structurally defined cutoffs, making it much more straightforward to detect target particles bearing a particular surface marker or biomarker on the downstream, sensing element 108.

Figure 7:
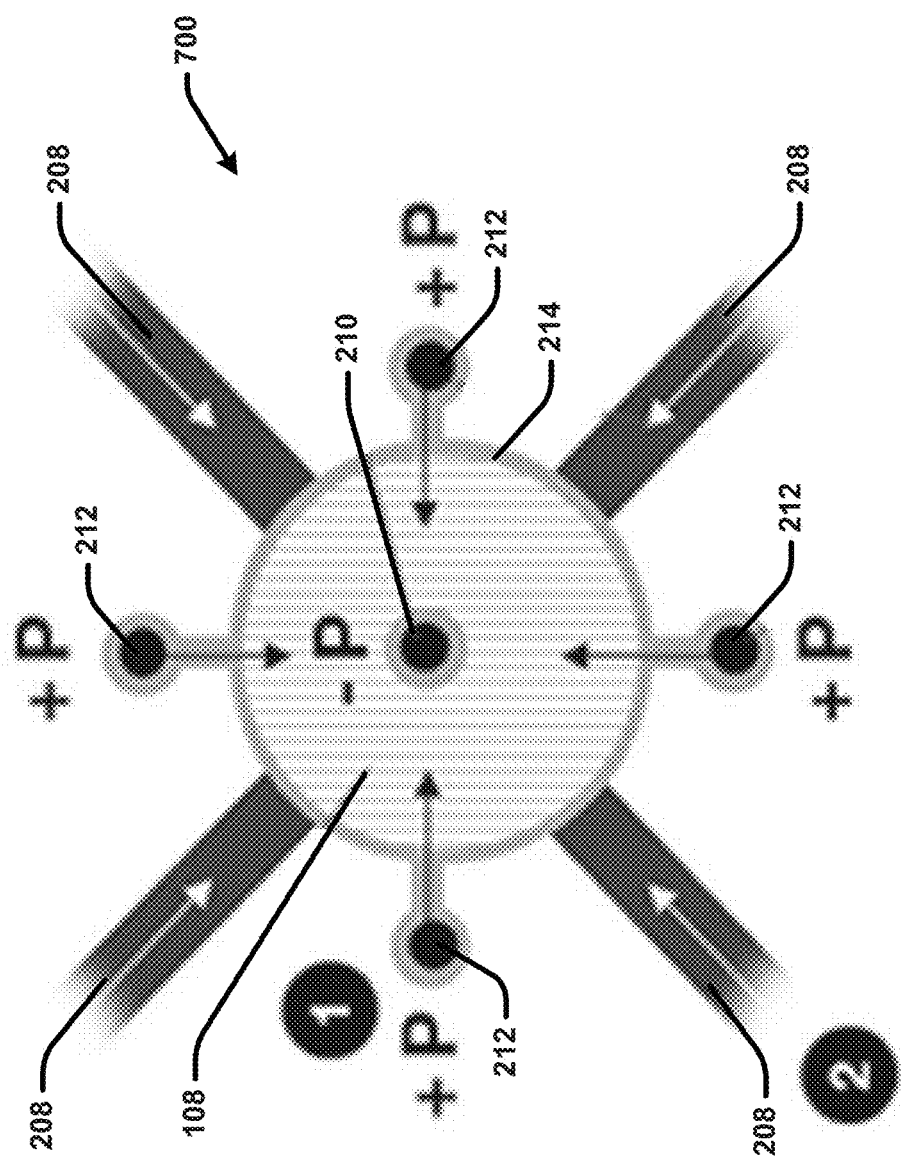
FIG. 7 illustrates an enlarged view of an example detection unit of an example microfluidic chip that integrates on-chip particle purification and biomarker detection functionality in accordance with one or more embodiments described herein.

FIG. 7 illustrates an enlarged view of an example detection unit 700 of an example microfluidic chip (e.g., microfluidic chip 106) that integrates on-chip particle purification and biomarker detection functionality in accordance with one or more embodiments described herein. Repetitive description of like elements employed in respective embodiments is omitted for sake of brevity.

The detection unit 700 can include the sensing element 108. In the embodiment shown, the detection unit 700 can also include the portion of the outlet bus 208 that connects to the sensing element 108 and provides for injecting a stream of buffer fluid comprising the purified or separated target particles onto and over the surface of the sensing element 108 coated with a surface chemistry (e.g., one or more specific molecules or macromolecules) that provides chemical specificity for one or more known biomarkers that may be present on or within the target particles. In this regard, the as discussed above, the sensing element 108 can facilitate detecting presence of one or more biomarkers by coating or otherwise providing one or more reactive agents that have a known chemical specificity for the one or more biomarkers, such as antibodies and aptamers known to bind with one or more surface markers. In one or more example implementations, the sensing element 108 can include one or more antibodies or aptamers known to bind with exosomes bearing a particular oncogenic surface marker (e.g. CD81, PSMA, etc.). The chemical specificity however is not limited to antibody/epitope interactions but can be extended to any specific chemical or biochemical interaction between two molecules or macromolecules, including naturally occurring and synthetic molecules/macromolecules. For example, the chemical interactions can include permanent covalent linkage as well as reversible bond interactions, such as electrostatic interactions, hydrophobic interactions, complementarity interactions and the like. In this regard, the sensing element 108 can provide for detecting biomarkers are result of interactions including but not limited to, antibody-epitope interactions, complementary DNA or RNA strand hybridization interactions, DNA binding proteins and DNA consensus sequence interactions, protein-protein interactions, protein-small molecule interactions, polymerization reactions, biotin-streptavidin interactions, and others.

The sensing element itself 108 can take on a variety of structures and materials to enhance the signal generated as a result of a chemical reaction between the surface chemistry of the sensing element and the one or more biomarkers. For example, the sensing element 108 can include an optical element that enhances a visual signal generated or detected in association with binding of a antibody provided on the surfaced of the sensing element with an epitope of a target particle, such as fluorescence signal of immuno-bound exosomes, thereby enhancing the sensitivity of the sensing element, In this regard, the sensing element 108 can include but is not limited to, a photonic grating or pillar array, an optoelectrical element, or a plasmonic structure.

The detection unit 700 can further include one or more third inlet vias 212 through which detection fluid including the reactive analyte substances can be introduced and applied to coat the surface of the sensing element 108. The detection unit 700 can also include a distribution bus 214 to facilitate evenly coating the sensing element with the introduced detection fluid. For example, in one or more embodiments, prior to introducing purified sample to the sensing element 108, the sensing element 108 can be coated with appropriate detection molecules/macromolecules (e.g., antibodies, aptamers, etc.) in accordance with a coating process (noted in FIG. 7 as coating step 1). With reference to FIGS. 2C-2D, FIG. 3C and FIG. 7, in accordance with the coating process, detection fluid (e.g., antibody-containing fluid) can be introduced through the one or more third inlet vias 212 by applying a positive pressure at these inlets, or more directly to the detection fluid reservoir 308 to which the one or more third inlet vias 212 are fluidically connected (e.g., via fluidic connections 212'). At the same time, a comparatively negative pressure can be applied at the global outlet via 210. The binding chemistry of the detection fluid can thus be forced to flow from one or more third inlet vias 212 to the global outlet via 210, thereby coating the sensing element 108. In some implementations, the sensing element can be pre-wetted prior to the coating step to facilitate the coating process. Once the sensing element 108 has been coated the separation-purification apparatus 100 is ready to use particle purification and separation. In this regard, in accordance with step 2, the upstream separation can then be performed in accordance with the techniques described herein, bringing the purified particles (e.g., exosomes) to the sensing element 108 by way of the outlet bus 208, where they can potentially bind to the sensing element 108 (if a particular target exosome and/or biomarker is present) and generate a reactionary signal that can be detected. For example, in some implementations, a target particle can be detected through immunocapture, producing a fluorescent signal that can be observed with fluorescence microscopy, and therefore manually detectable by eye or through software to automate the process.

Figure 8:
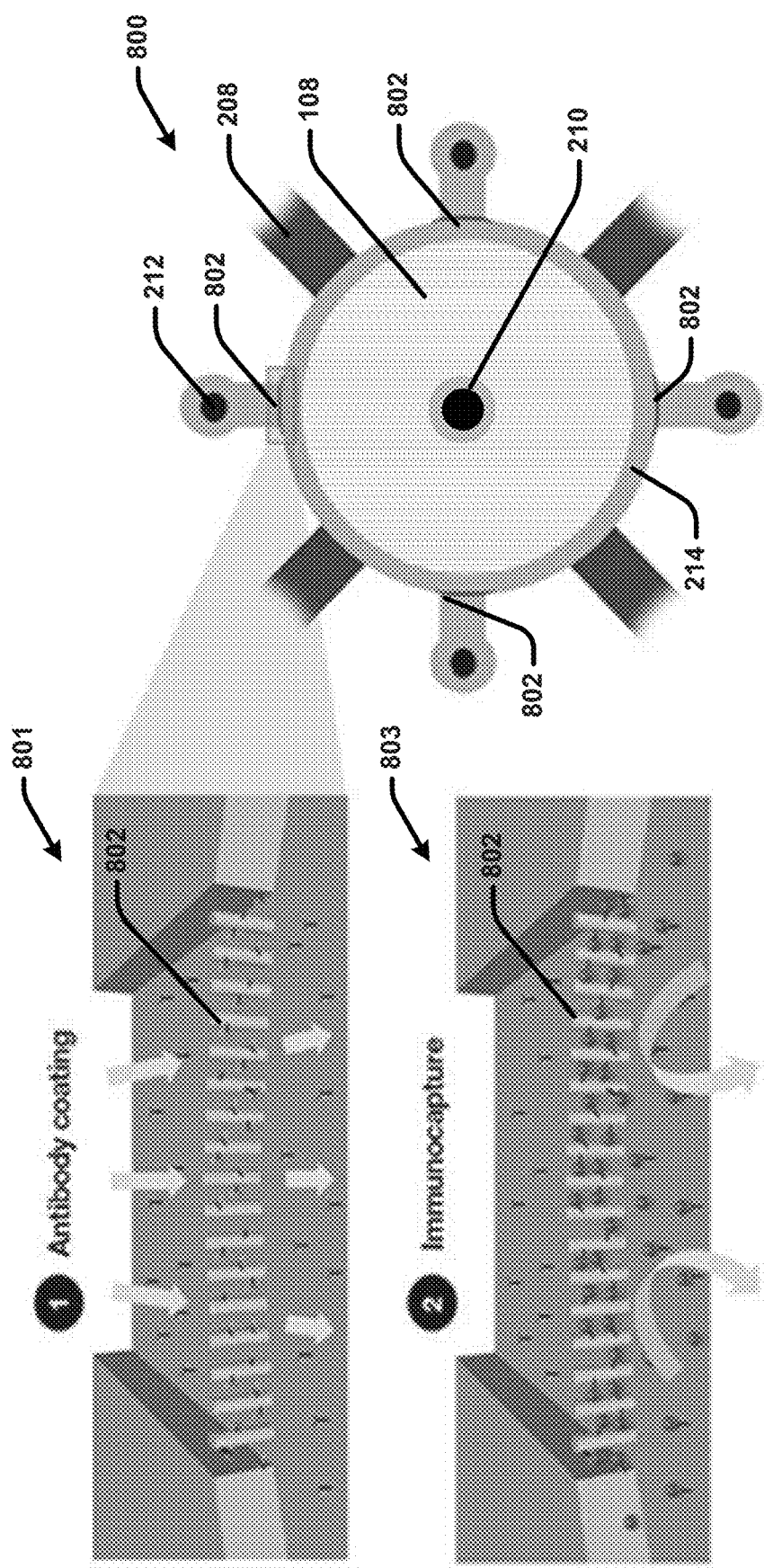
FIG. 8 illustrates an enlarged view of another example detection unit of an example microfluidic chip that integrates a blocking element in accordance with one or more embodiments described herein.

FIG. 8 illustrates an enlarged view of another example detection unit 800 of an example microfluidic chip (e.g., microfluidic chip 106) that integrates on-chip particle purification and biomarker detection functionality in accordance with one or more embodiments described herein. Repetitive description of like elements employed in respective embodiments is omitted for sake of brevity.

Detection unit 800 can include same or similar features and functionality as detection unit 700 with the addition of a blocking element 802 at the inlet interface between the one or more third inlet vias 212 and the sensing element 108, (e.g., including openings where the detection fluid can flow from the one or more second inlet vias onto the surface of the sensing element 108. The primary function of the blocking element 802 is to block free floating, unbound or unreacted target particles (e.g., exosomes), from reversely flowing away from the sensing element 108 and the global outlet via 210 toward the one or more third inlet vias 212. In some implementations, in which detection molecules are not tethered to or become separated from the surface of the sensing element, the blocking element 802 can also prevent reverse flow of free floating reacted molecular complexes (e.g., antibody-exosome complexes) through the third inlet vias 212. In this regard, the blocking element 802 can include a physical structure that prevents essentially any particles other than free floating detection molecules/macromolecules (which are generally very small) therethrough. The blocking element 802 can thus corral isolated target biological entities (e.g. exosomes, viruses, etc.) with biochemically specific markers within the field of view of an optical detector. For example, as shown in call out boxes 801 and 803, in one embodiment, the blocking element 802 can comprise integrated pillars, a sieve, or the like, with gaps in between them at the perimeter of the sensing element 108 and adjacent to the detection fluid chemistry inlets. The gaps can be too small for free-flowing isolated target particles (e.g., exosomes) to fit through, but large enough for the coating chemistry to flow through (e.g., antibodies in the example shown). In this way, the blocking element can prevent loss of exosomes bearing the target surface proteins, or epitopes, keeping them contained completely within the field of view and surface of the sensing element 108.

FIG. 9A illustrates an enlarged view of another example detection unit 900 that can be employed in a microfluidic chip (e.g., microfluidic chip 106) that integrates on-chip particle purification and biomarker detection functionality in accordance with one or more embodiments described herein. Detection unit 900 can include same or similar features and functionality as detection unit 800, with the addition of a plurality of different detection chambers to the sensing element 108. Repetitive description of like elements employed in respective embodiments is omitted for sake of brevity.

In the embodiment shown, the sensing element 108 can be subdivided into a plurality of separate detection chambers, respectively identified as detection chambers 901, 902, 903 and 904. Each of the different detection chambers can provide for detecting a presence of different biomarker and/or target particle. For example, each (or in some implementations one or more) of the detection chambers 901, 902, 903 and 904 can be coated with different detection molecules/macromolecules known to react with different biomarkers. For instance, the respective detection chambers can be coated with different biomarker-specific antibodies or aptamers. With these embodiments, the sensing element 108 can provide for simultaneous detection of a plurality of potential biomarkers from a single input fluid sample and with a single purification-detection procedure. Simultaneous detection of multiple markers allows for fast, and effective diagnosis of various diseases, such as certain forms of cancer. In order to ensure isolation between the different detection chambers, the detection chambers can respectively be separated from one another via partition wall 906.

In accordance with this embodiment, a separate detection fluid should be injected into each of the respective detection chambers in isolation. In this regard, each of the detection chambers can employ a different inlet via (of the one or more third inlet vias 212) that can respectively be fluidically coupled to different detection fluid reservoirs (e.g., as opposed to the single, communal, detection fluid reservoir 308, shown in FIGS. 3A-3C). For example, as shown in FIG. 9B, rather than a communal, detection fluid reservoir 308, reservoir layer (included in the bottom plate 102B or between the bottom plate 102B and the microfluidic chip 106) can include a plurality of isolated detection fluid reservoirs or channels 910 through which the different detection fluids can be injected to coat the different detection chambers.

Figure 9C:
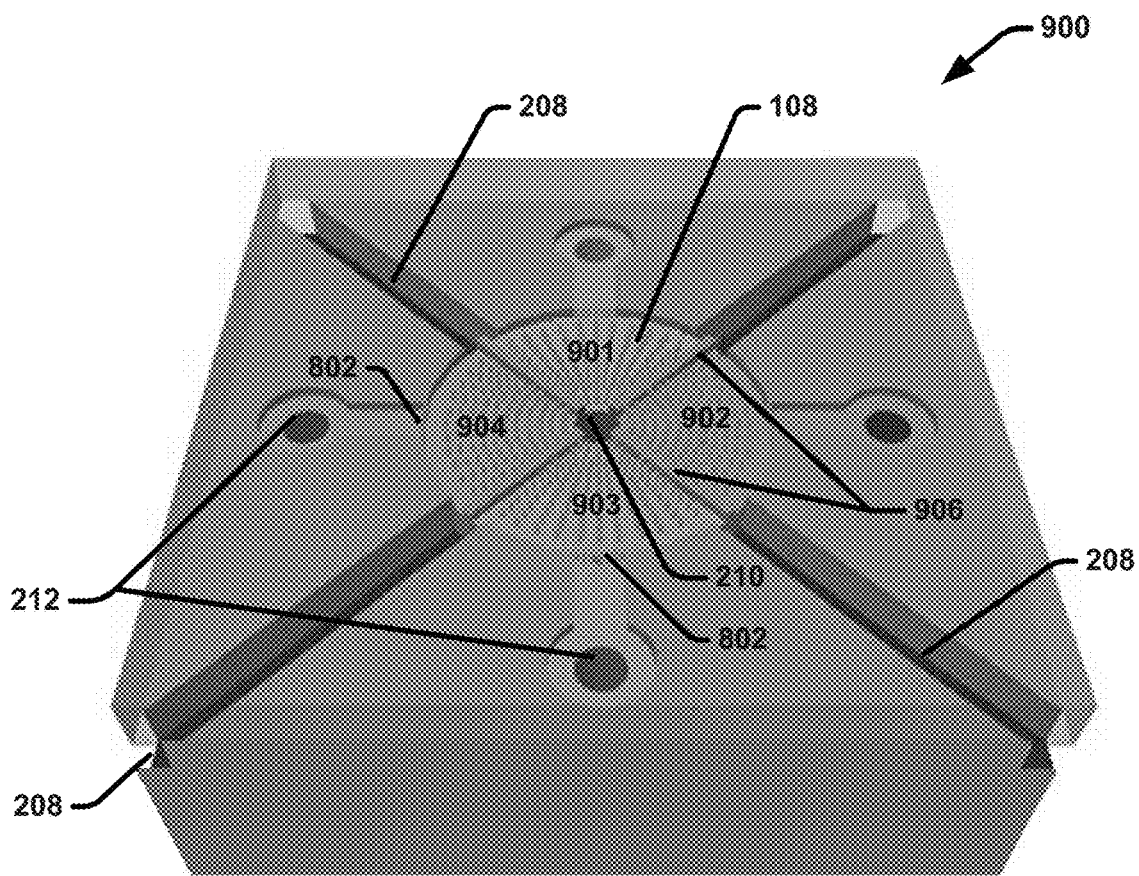
FIGS. 9C-9D present a 3D, perspective view of another example detection unit of a microfluidic chip that integrates on-chip particle purification and biomarker detection functionality in accordance with one or more embodiments described herein.
Figure 9D:
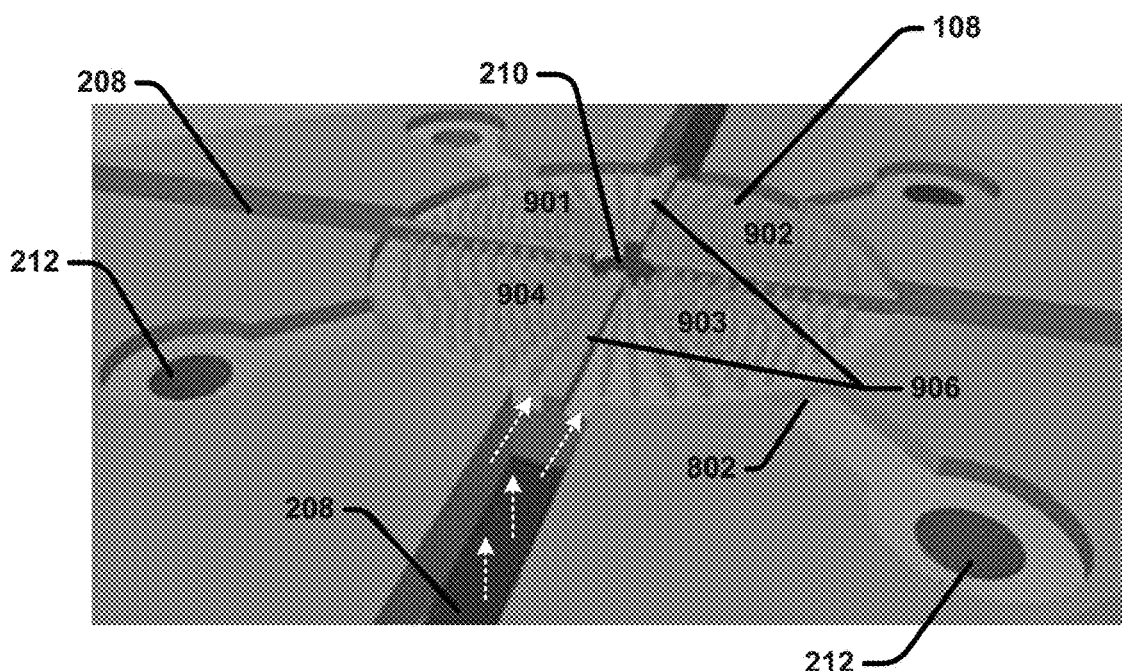

FIGS. 9C and 9D present a 3D, perspective view of example detection unit 900 in accordance with one or more embodiments described herein. With reference to FIGS. 2C and 2D in conjunction with reference to FIGS. 9C and 9D, detection unit 900 can include same or similar features and functionalities as detection unit 200 with the addition of separate detection chambers 901, 902, 903 and 904 to the sensing element 108. The respective detection chambers are separated by separation walls 906. In addition, a blocking element 802 is formed at the inlet region between the respective third inlet vias 212 and the sensing element 108. As shown in FIG. 9D with reference to the dashed arrow lines, after the different detection chambers of the sensing element 108 have been functionalized with a different surface chemistry, a stream of buffer fluid comprising purified target particles can flow from the separation unit 206, up through the outlet bus 208 channels and onto the sensing element 108. In the embodiment shown, a single outlet bus 208 channel can feed two detection chambers at a time (e.g., detection chambers 903 and 904 in the demonstrated example).

Figure 10:
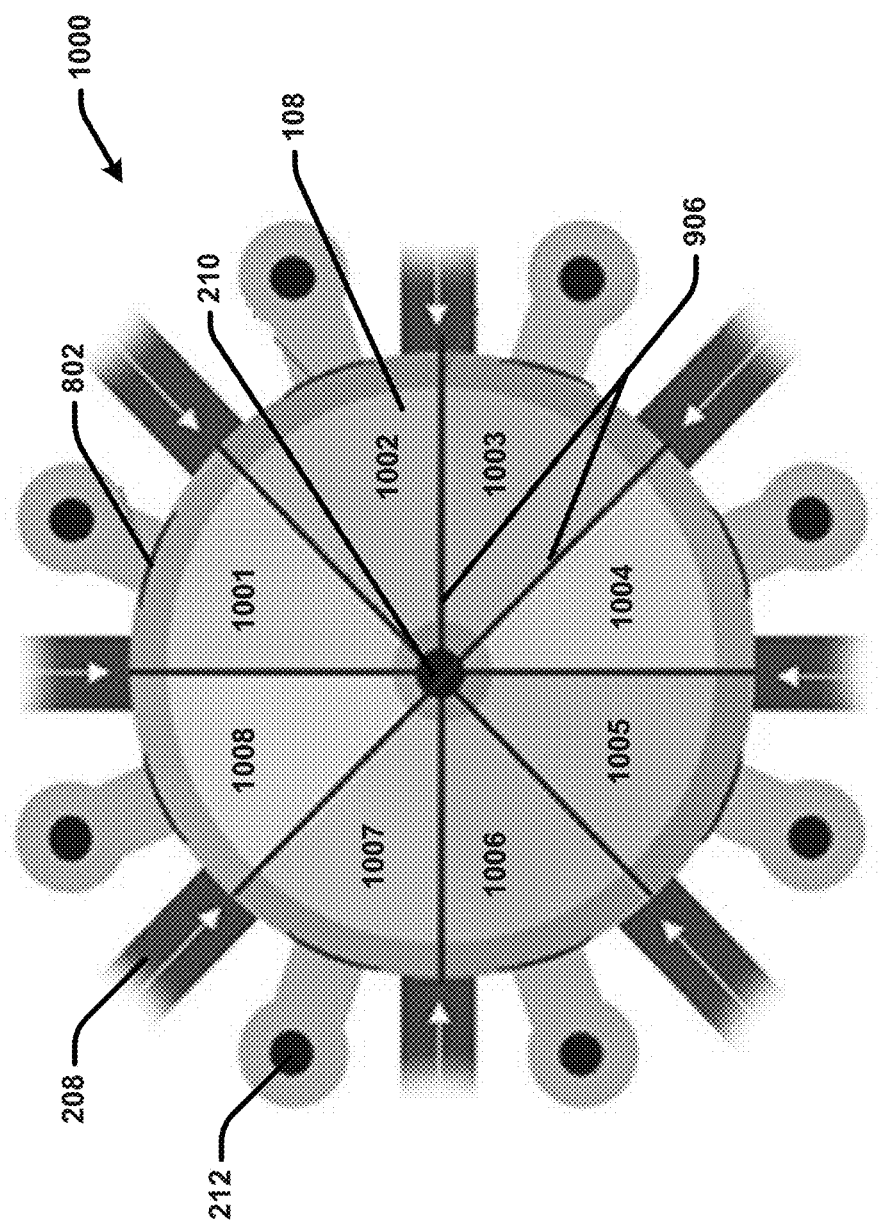
FIG. 10 illustrates an enlarged view of another example detection unit of an example microfluidic chip that integrates on-chip particle purification and biomarker detection functionality in accordance with one or more embodiments described herein.

FIG. 10 illustrates an enlarged view of another example detection unit 1000 that can be employed in a microfluidic chip (e.g., microfluidic chip 106) that integrates on-chip particle purification and biomarker detection functionality in accordance with one or more embodiments described herein. Detection unit 1000 can include same or similar features and functionalities as detection unit 900 with the addition of a greater number of detection chambers, including detection chambers 1001-1008. In this regard, the number of detection chambers in which the sensing element is subdivided into can vary and is not limited to one, four or eight (as in the embodiments shown). However, as the number of detection units increases, the number of third inlet vias 212 will also increase, as each detection unit can comprise a separate injection via (and corresponding channel and/or reservoir) through which each different type of detection fluid chemistry can be provided. Repetitive description of like elements employed in respective embodiments is omitted for sake of brevity.

Figure 11:
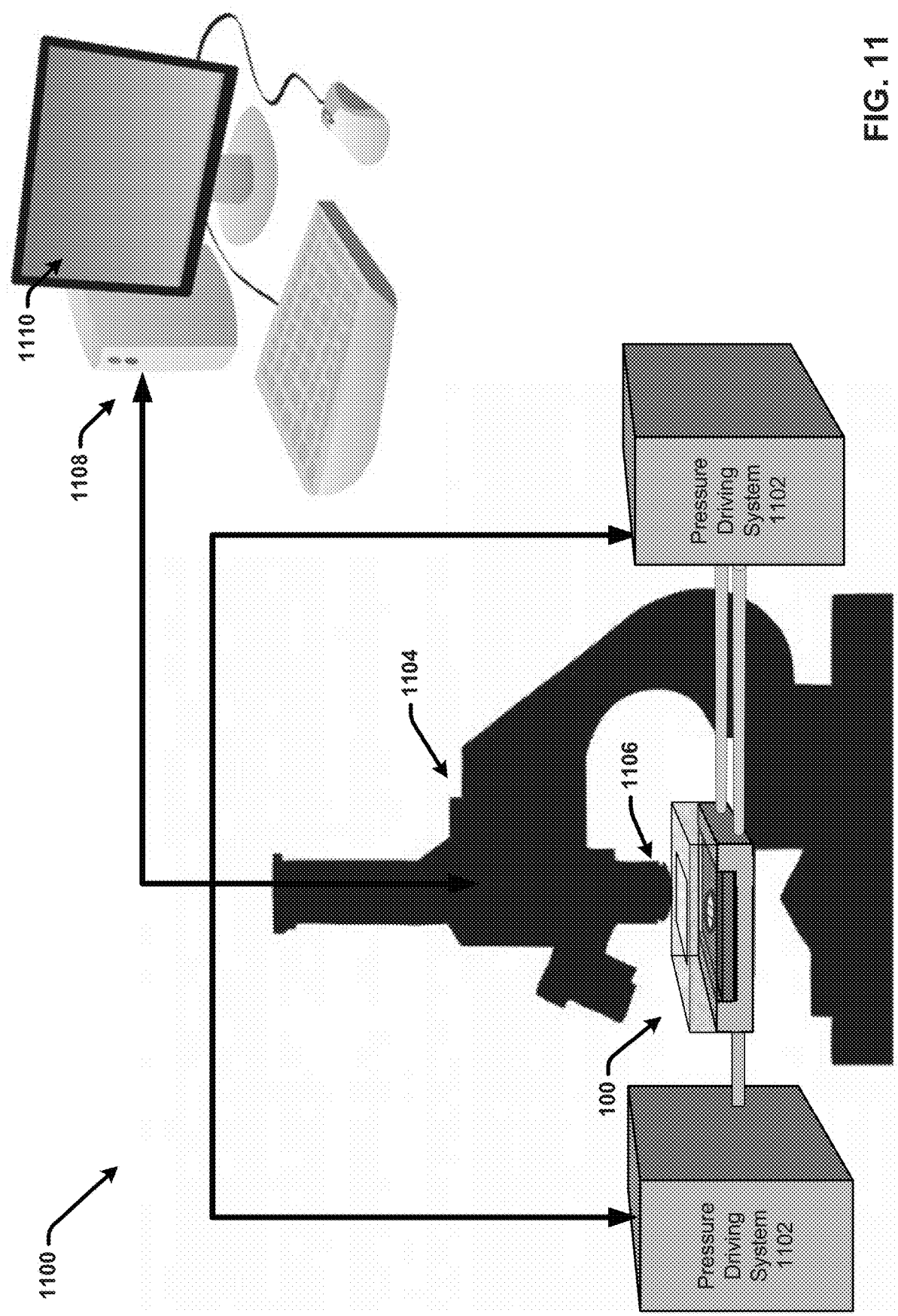
FIG. 11 illustrates an example system that facilitates integrating real-time particle purification and biomarker detection in accordance with one or more embodiments described herein.

FIG. 11 illustrates an example system 1100 that facilitates integrating real-time particle purification and biomarker detection in accordance with one or more embodiments described herein. Embodiments of systems (e.g., system 1100 and pressure driving system 1102), imaging devices (e.g., imaging device 1104) and computing devices (e.g., computing device 1108) described herein can include one or more machine-executable components embodied within one or more machines (e.g., embodied in one or more computer readable storage media associated with one or more machines). Such components, when executed by the one or more machines (e.g., processors, computers, computing devices, virtual machines, etc.) can cause the one or more machines to perform the operations described. Repetitive description of like elements employed in respective embodiments is omitted for sake of brevity.

System 1100 includes separation-purification apparatus 100, a pressure driving system 1102 an imaging device 1104 and a computing device 1108. The computing device 1108 can be communicatively coupled to the imaging device 1104 and/or the pressure driving system 1102 via one or more wires and/or one or more wireless networks (e.g., a local area network (LAN), a wide area network (WAN), such as the Internet, and the like).

The pressure driving system 1102 can be operatively coupled to one or more inlet ports and outlet ports of the housing (e.g., which can be or correspond to a microfluidic flow cell or the like) to control flow of the various fluids (e.g., the biological sample fluid, the buffer fluid, the detection fluid, and other potential cleaning/preparation fluids) into, out of, and through the housing 102 and the microfluidic chip 106. For example, in some implementations, after the above noted fluids are introduced into the designated reservoirs of the housing 102 (e.g., via pipetting or another suitable technique), the apparatus can be operatively coupled to the pressure driving system 1102 and while also being aligned with the imaging device 1104. In some implementations, the imaging device 1104 and the pressure driving system 1102 can be a combined system. In other implementation, the pressure driving system 1102 can facilitate injecting the various fluids into the corresponding reservoirs of the housing 102 prior to and/or at runtime of the apparatus. The pressure-driving system can be a fully automated pressure driving machine, a manually operated pressure driving machine, or a combination thereof. The pressure driving system can form a pressure seal between the inlet ports (e.g., inlet port 112, inlet port 114, and inlet port 116) and the respective reservoirs, channels, inlets, etc., of the housing 102, and/or the respective outlet ports (e.g., outlet port 118 and outlet port 120). In this regard, the pressure driving system can apply pressure to initiate fluid flow of one or more fluids within the different fluid reservoirs located within the housing and a reservoir comprising the biological sample fluid, referred to herein as the sample fluid reservoir.

The imaging device 1104 can comprise a lens 1006 or capture region that is aligned with the sensing element 108. In this regard, the location of the sensing element 108 at or near the center of the microfluidic chip 106 (with a transparent window formed thereover as part of the capping layer 110), can enable efficient optical readout of biochemically specific information that developed or captured by the sensing element (e.g., immunocaptured exosomes detected using for example fluorescence microscopy). In the embodiment shown, the imaging device 1104 is a microscope. In some implementations in which the imaging device 1104 comprises a microscope, the microscope can be or include a fluorescence microscope configured to capture immunofluorescent signals generated by fluorescent labeled molecules (e.g., antibodies or aptamers, target particles, binding proteins, etc.) captured by the sensing element 108. The features and functionalities of the microscope can however vary. The imaging device 1104 can alternatively or additionally include other types of imagining devices or cameras configured to captures still images, 2D images, high dynamic range images, video, etc. of the sensing element 108 at various stages of operation of separation-purification apparatus 100 in accordance with the techniques described herein (e.g., in real-time during separation and detection flow or after completion of running of the biological fluid sample therethrough). In some implementations, these images can be sent to a computing device 1108 for rendering via a display 1110 of the computing device 1108. In this regard, in some implementations, biomarker detection and/or biochemical analysis of target particles with specific surface markers (e.g., exosomes with specific carcinogenic surface markers) can be manually performed by examining the sensing element 108 through the microscope and/or via image data presented via the display 1110 in real-time during separation and detection flow, or after completion of running of the biological fluid through the apparatus. In other implementations, described infra, the computing device 1108 can include software configured to perform automated biomarker detection and analysis based on image data captured of the sensing element 108 before, during, and/or after running of biological fluid sample through separation-purification apparatus 100.

Figure 12:
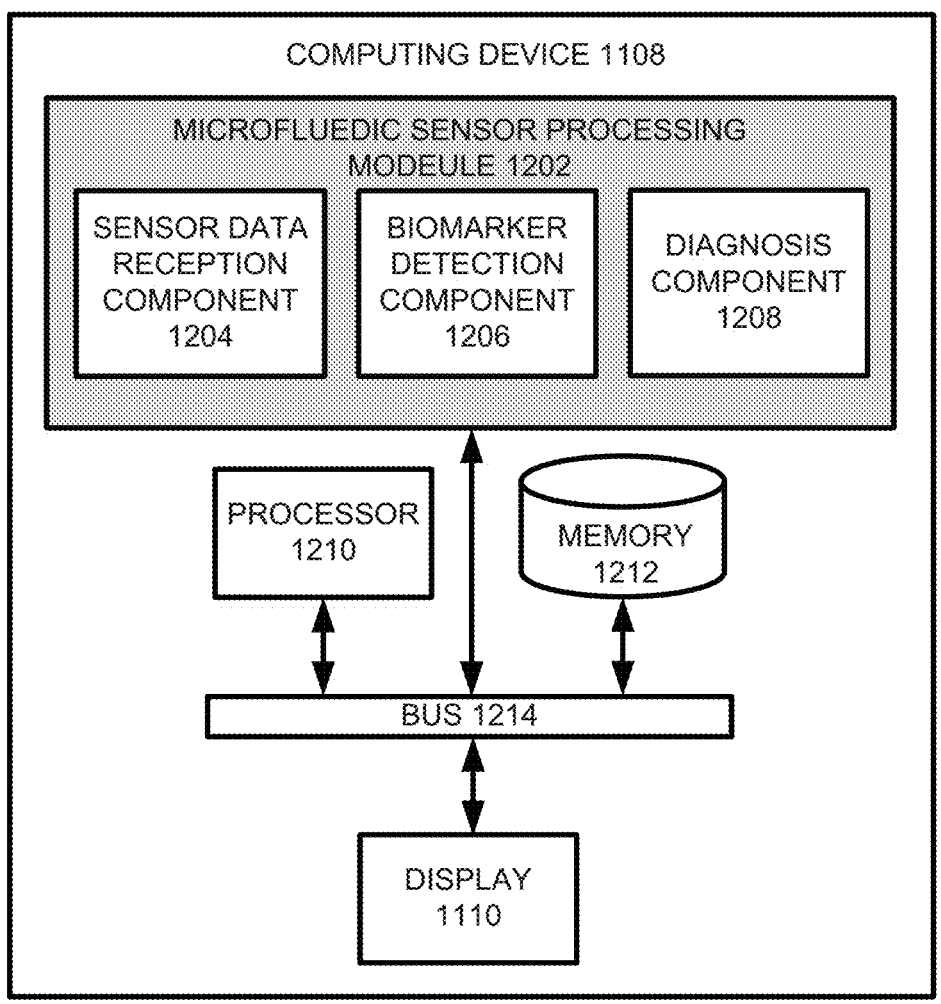
FIG. 12 illustrates an example computing device that facilitates real-time biomarker detection and analysis in accordance with one or more embodiments described herein.

FIG. 12 illustrates an example computing device 1108 that facilitates real-time biomarker detection and analysis in accordance with one or more embodiments described herein. Repetitive description of like elements employed in respective embodiments is omitted for sake of brevity.

As presented in system 1100, the computing device 1108 can include or be operatively coupled to a display 1110 via which image data captured of the sensing element 108 can be rendered. The computing device 1108 further includes or can be operatively coupled to at least one memory 1212 and at least one processor 1210. In various embodiments, the at least one memory 1212 can store executable instructions that when executed by the at least one processor 1210, facilitate performance of operations defined by the executable instruction. For example, in the embodiment shown, the computing device 1108 further include microfluidic sensor processing module 1202 which includes sensor data reception component 1204, biomarker detection component 1206, and diagnosis component 1208. In one or more embodiments, these components (e.g., the microfluidic sensor processing module 1202 and additional components of the microfluidic sensor processing module 1202) can be stored in memory 1212 and executed by the at least one processor 1210. The computing device 1108 can further include a device bus 1214 that communicatively couples the various components of the computing device 1108 (e.g., the microfluidic sensor processing module 1202, the processor 1210, the memory 1212 and the display 1110). Examples of said processor 1210 and memory 1212, as well as other suitable computer or computing-based elements, can be found with reference to FIG. 16, and can be used in connection with implementing one or more of the systems or components shown and described in connection with FIGS. 11 and 12 or other figures disclosed herein.

The microfluidic sensor processing module 1202 can facilitate various processing functionalities associated with evaluating chemical reactions that occur (or do not occur) at the sensing element 108 of the disclosed microfluidic chips. In this regard, the sensor data reception component 1204 can receive data regarding the chemical reaction that occur (or do not occur) at a particular sensing element in association with flow of purified target biological entities over the surface of a functionalized sensing element. In various embodiments, this data can include image data captured of the sensing unit before, during, and/or after flow process. For example, the image data can include still images of the sensing element 108 captured by an imaging device (e.g., imaging device 1104) positioned in line-of-sight of the sensing element at one or more points before, during and/or after the flow process. In other implementations, the image data can include video captured during the flow process by such an imaging device. With these implementations, the microfluidic sensor processing module 1202 can provide for real-time or live biomarker detection and analysis. In some embodiments, the chemical reactions that occur at the sensing element 108 between a target particle or target biomarker and the one or more detection molecules/macromolecules with which the sensing element 108 is functionalized can result in other forms of detectable sensory data, other than visual signals. For example, in some implementations, a chemical reaction can be detected by generation of a detectable electrochemical signal, generation a heat signal, or another form of sensory data. With these implementations, the sensor data reception component 1204 can receive information regarding generation of such other types of sensory signals to facilitate biochemical analysis.

The biomarker detection component 1206 can analyze received sensory data (e.g., image data, or another form of sensory data) captured of and/or generated at the sensing element regarding occurrence, (or non-occurrence), of one or more chemical reactions between one or more particles in the purified biological sample stream and one or more detection molecules/macromolecules of the sensing element 108, and determine whether a particular biomarker is present. In some implementations, the biomarker detection component 1206 can also determine a quantitative measure of the amount of detected biomarker. In this regard, the biomarker detection component 1206 can access and/or employ biomarker identification information (e.g., stored in memory) that correlates potential chemical reaction-based image signals that can be generated at a sensing element (e.g., based on the type of detection molecules/macromolecules with which the sensing element is functionalized), with known biomarkers and/or known particles. The biomarker detection component 1206 can further be configured to identify or otherwise recognize an image signal that correlates with a known biomarker or particle to determine whether the biomarker is present. For example, in some implementations, the image signals can include image data such, as fluorescent image data, that visually tags a chemical bond between a target biomarker or surface marker and a detection molecule/macromolecule. In other implementation, the image signal data can include a particular coloration or change in coloration, a particular brightness or change in brightness, a particular image pattern, and the like. In various embodiments, based on the analysis of the received sensory data (e.g., image data) the biomarker detection component 1206 can generate biomarker information (for rendering via the display or for otherwise providing to an entity via a suitable output device) identifying detected biomarkers and/or particles, and in some implementations, an amount of the detected biomarkers and/or particles.

The diagnosis component 1208 can further analyze biomarker information to determine diagnosis information regarding a disease state or medical condition of the entity (e.g., a patient) from which the biological fluid sample was taken. In this regard, the diagnosis component 1208 can access and employ information that correlates known biomarkers, known biomarker amounts, and/or known biomarker combinations (in implementations in which two or more biomarkers can be detected at a time, such as with respect to detection unit 200, detection unit 800, detection unit 900, detection unit 1000 and the like), with particular diseases, disease states, and/or medical conditions, to determine whether a disease, disease state, and/or medical condition has been detected.

Figure 13:
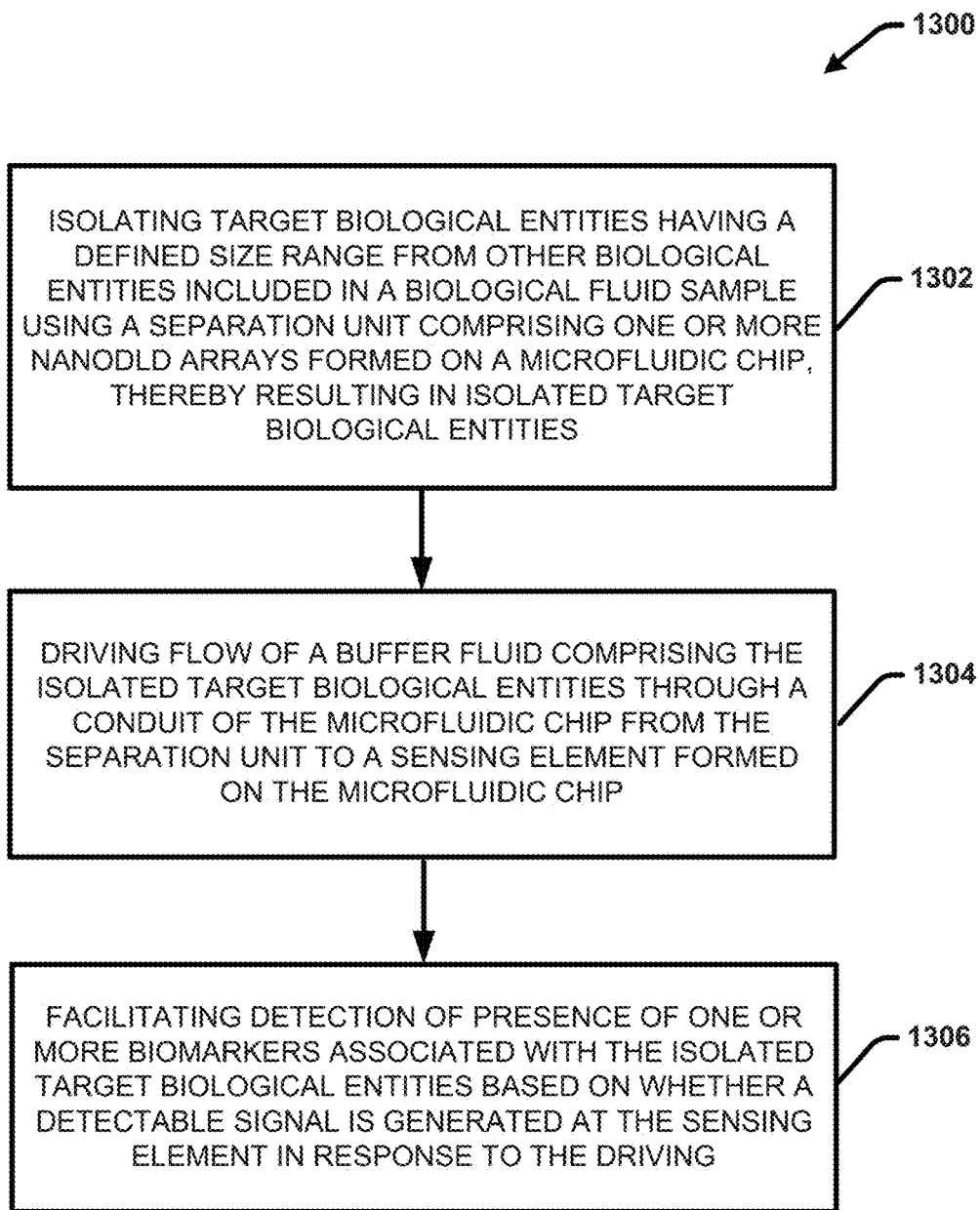
FIG. 13 illustrates a flow diagram of an example, non-limiting method for performing particle purification and biomarker detection using an integrated microfluidic device in accordance with one or more embodiments described herein.

FIG. 13 illustrates a flow diagram of an example, non-limiting method 1300 for performing particle purification and biomarker detection using an integrated microfluidic device in accordance with one or more embodiments described herein. Repetitive description of like elements employed in respective embodiments is omitted for sake of brevity.

At 1302, target biological entities having a defined size range are isolated from other biological entities included in a biological fluid sample using a separation unit (e.g., separation unit 206) comprising one or more nanoDLD arrays formed on a microfluidic chip (e.g., microfluidic chip 106), thereby resulting in isolated target biological entities. At 1304 buffer fluid comprising the isolated target biological entities is driven through a conduit (e.g., outlet bus 208) of the microfluidic chip from the separation unit to a sensing element (e.g., sensing element 108) formed on the microfluidic chip. At 1306, detection of the presence of one or more biomarkers associated with the isolated target biological entities is facilitated based on whether a detectable signal is generated at the sensing element in response to the driving.

Figure 14:
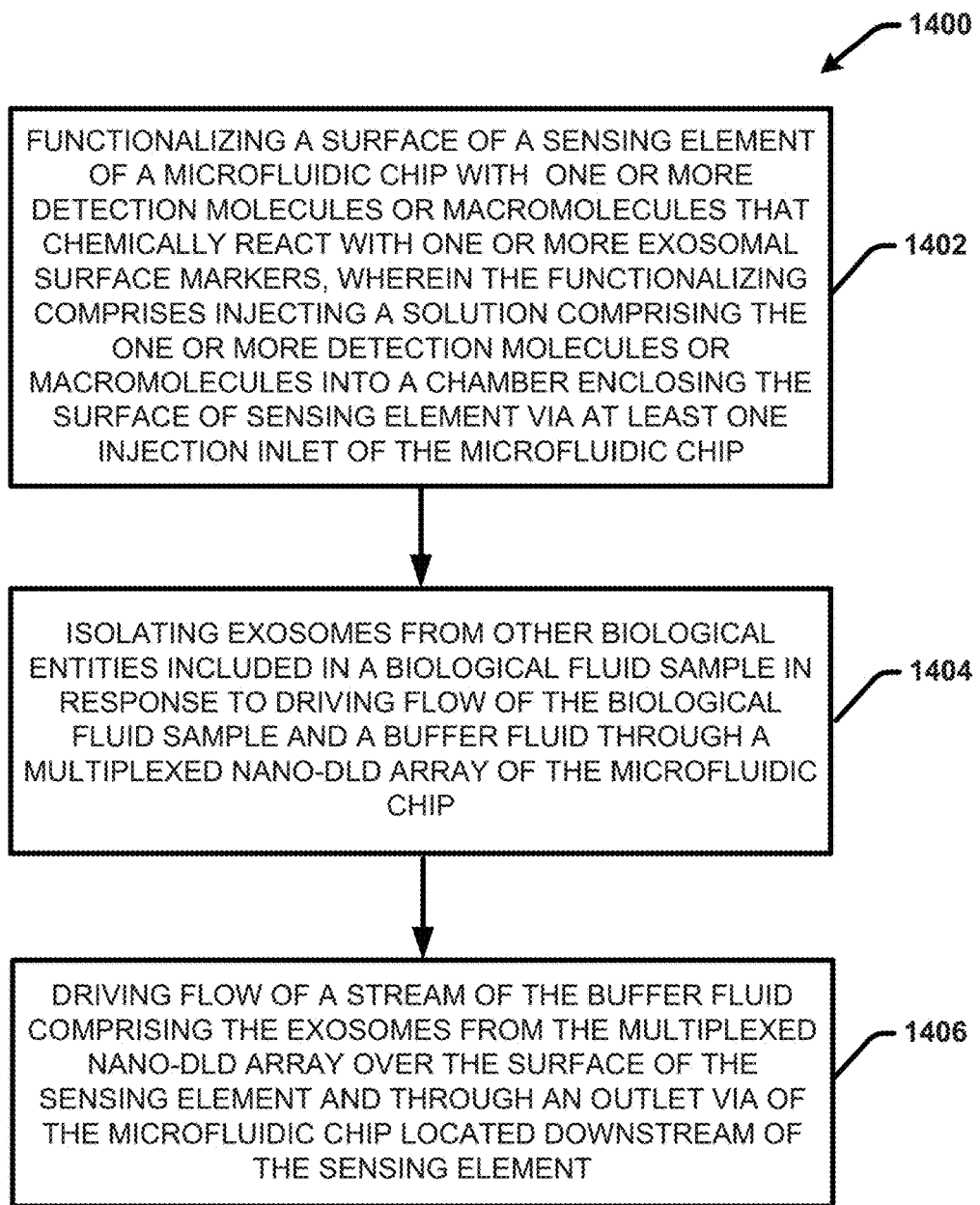
FIG. 14 illustrates a flow diagram of an example, non-limiting method for functionalizing a sensing element of an integrated microfluidic device and thereafter, employing the integrated microfluidic device to isolate exosomes and detect presence of exosomal surface markers based on reaction with the functionalized sensing element, in accordance with one or more embodiments described herein.

FIG. 14 illustrates a flow diagram of an example, non-limiting method 1400 for functionalizing a sensing element of an integrated microfluidic device and thereafter, employing the integrated microfluidic device to isolate exosomes and detect presence of exosomal surface markers based on reaction with the functionalized sensing element, in accordance with one or more embodiments described herein. Repetitive description of like elements employed in respective embodiments is omitted for sake of brevity.

At 1402, functionalizing a surface of a sensing element (e.g., sensing element 108) of a microfluidic chip (e.g., microfluidic chip 106) with one or more detection molecules or macromolecules (e.g., antibodies, aptamers, etc.) that chemically react with one or more exosomal surface markers, wherein the functionalizing comprises injecting a solution comprising the one or more detection molecules or macromolecules into a chamber enclosing the surface of sensing element via at least one injection inlet (e.g., the one or more third inlet vias 212) of the microfluidic chip. At 1404, exosomes are isolated from other biological entities included in a biological fluid sample in response to driving flow of the biological fluid sample and a buffer fluid through a multiplexed nanoDLD array (e.g., nanoDLD array 506) of the microfluidic chip. At 1406, a stream of the buffer fluid comprising the exosomes is driven from the multiplexed nanoDLD array (e.g., via outlet bus 208) over the surface of the sensing element and through an outlet via (e.g., global outlet via 210) of the microfluidic chip located downstream of the sensing element.

Figure 15:
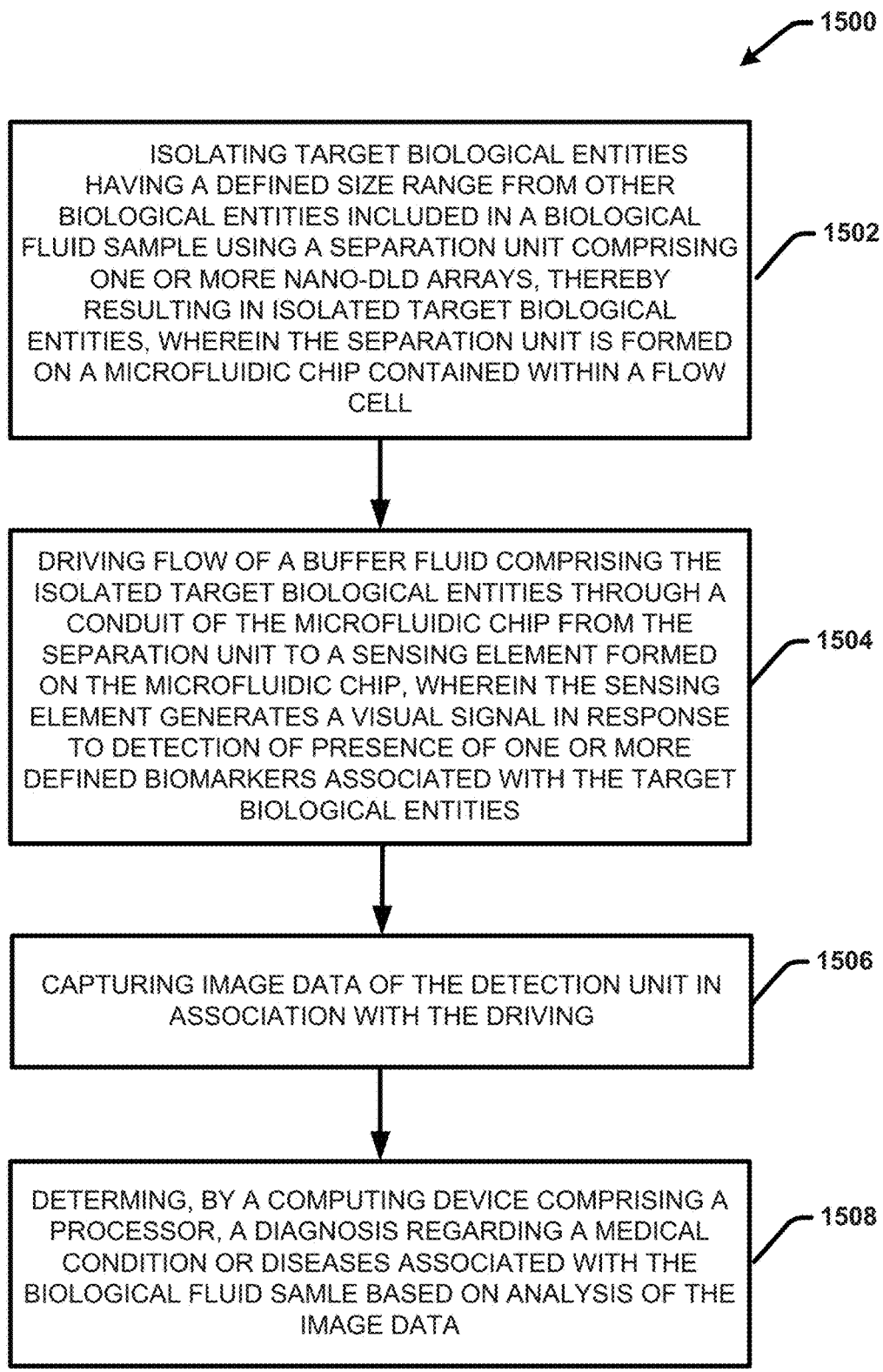
FIG. 15 illustrates a flow diagram of an example, non-limiting method that facilitates integrating real-time particle purification and biomarker detection in accordance with one or more embodiments described herein.

FIG. 15 illustrates a flow diagram of an example, non-limiting method 1500 that facilitates integrating real-time particle purification and biomarker detection in accordance with one or more embodiments described herein. Repetitive description of like elements employed in respective embodiments is omitted for sake of brevity.

At 1502, target biological entities having a defined size range from other biological entities included in a biological fluid sample are isolated using a separation unit comprising one or more nanoDLD arrays (e.g., separation unit 206), thereby resulting in isolated target biological entities, wherein the separation unit is formed on a microfluidic chip contained within a housing (e.g., housing 102). At 1504, a buffer fluid comprising the isolated target biological entities is driven through a conduit of the microfluidic chip (e.g., outlet bus 208) from the separation unit to a sensing element (e.g., sensing element 108) formed on the microfluidic chip, wherein the sensing element generates a visual signal in response to detection of presence of one or more defined biomarkers associated with the target biological entities. At 1506, image data of the detection unit is captured in association with the driving (e.g., via imaging device 1104). At 1508, a computing device comprising a processor (e.g., computing device 1108) determines a diagnosis regarding a medical condition or a disease state associated with the biological fluid sample based on analysis of the image data (e.g., using biomarker detection component 1206 and/or diagnosis component 1208).

Figure 16:
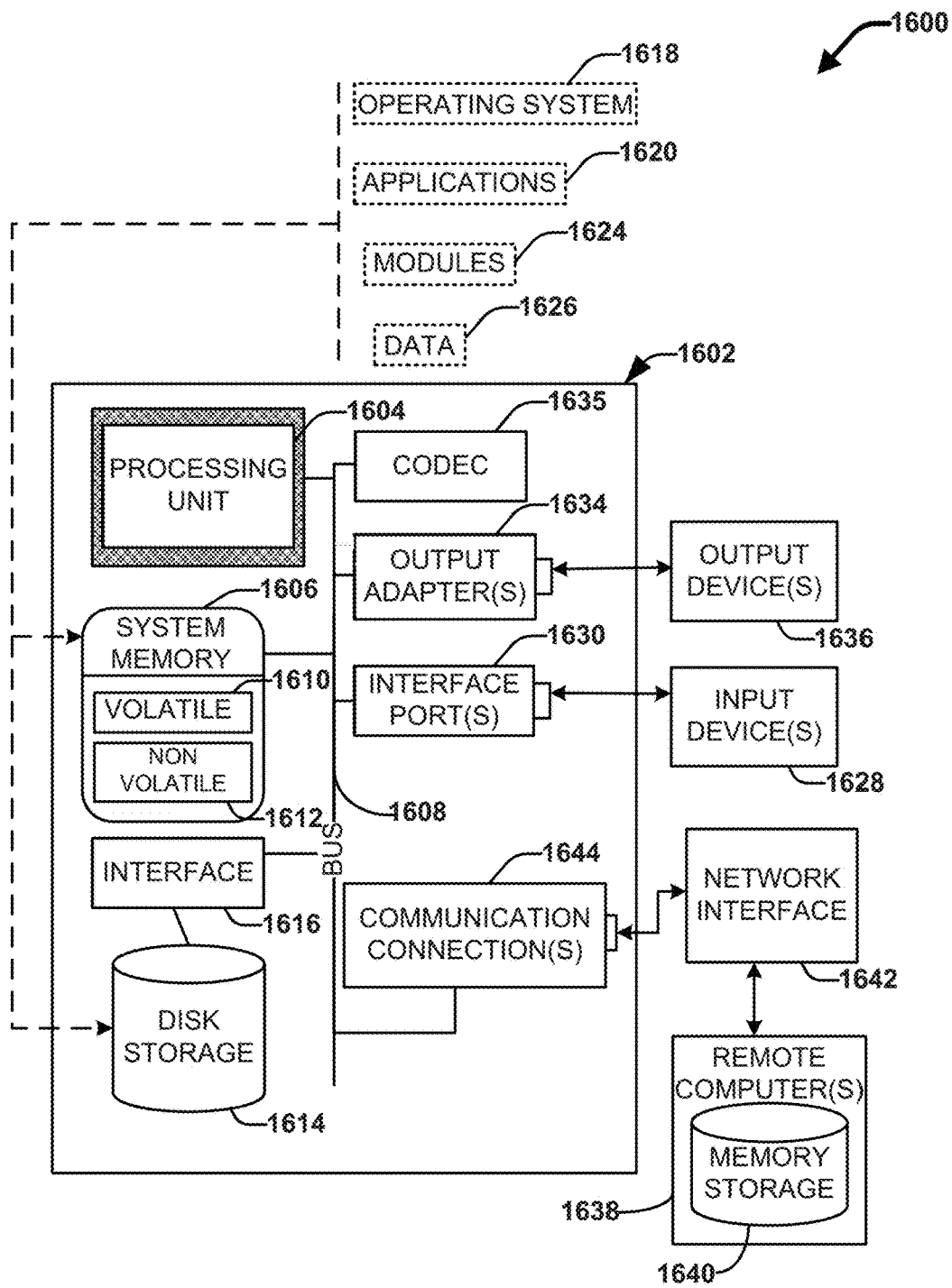
FIG. 16 illustrates a block diagram of an example, non-limiting operating environment in which one or more embodiments described herein can be facilitated.

In order to provide a context for the various aspects of the disclosed subject matter, FIG. 16 as well as the following discussion are intended to provide a general description of a suitable environment in which the various aspects of the disclosed subject matter can be implemented. FIG. 16 illustrates a block diagram of an example, non-limiting operating environment 1600 in which one or more embodiments described herein can be facilitated. For example, the operating environment 1600 can comprise and/or otherwise facilitate one or more features of the pressure driving system 1102, the imaging device 1104, and/or the computing device 1108 described herein in accordance with one or more embodiments. Repetitive description of like elements employed in other embodiments described herein is omitted for sake of brevity.

With reference to FIG. 16, a suitable operating environment 1600 for implementing various aspects of this disclosure can include a computer 1612. The computer 1612 can also include a processing unit 1614, a system memory 1616, and a system bus 1618. The system bus 1618 can operably couple system components including, but not limited to, the system memory 1616 to the processing unit 1614. The processing unit 1614 can be any of various available processors. Dual microprocessors and other multiprocessor architectures also can be employed as the processing unit 1614. The system bus 1618 can be any of several types of bus structures including the memory bus or memory controller, a peripheral bus or external bus, and/or a local bus using any variety of available bus architectures including, but not limited to, Industrial Standard Architecture (ISA), Micro-Channel Architecture (MSA), Extended ISA (EISA), Intelligent Drive Electronics (IDE), VESA Local Bus (VLB), Peripheral Component Interconnect (PCI), Card Bus, Universal Serial Bus (USB), Advanced Graphics Port (AGP), Firewire, and Small Computer Systems Interface (SCSI). The system memory 1616 can also include volatile memory 1620 and nonvolatile memory 1622. The basic input/output system (BIOS), containing the basic routines to transfer information between elements within the computer 1612, such as during start-up, can be stored in nonvolatile memory 1622. By way of illustration, and not limitation, nonvolatile memory 1622 can include read only memory (ROM), programmable ROM (PROM), electrically programmable ROM (EPROM), electrically erasable programmable ROM (EEPROM), flash memory, or nonvolatile random access memory (RAM) (e.g., ferroelectric RAM (FeRAM). Volatile memory 1620 can also include random access memory (RAM), which acts as external cache memory. By way of illustration and not limitation, RAM is available in many forms such as static RAM (SRAM), dynamic RAM (DRAM), synchronous DRAM (SDRAM), double data rate SDRAM (DDR SDRAM), enhanced SDRAM (ESDRAM), Synchlink DRAM (SLDRAM), direct Rambus RAM (DRRAM), direct Rambus dynamic RAM (DRDRAM), and Rambus dynamic RAM.

Computer 1612 can also include removable/non-removable, volatile/non-volatile computer storage media. FIG. 16 illustrates, for example, a disk storage 1624. Disk storage 1624 can also include, but is not limited to, devices like a magnetic disk drive, floppy disk drive, tape drive, Jaz drive, Zip drive, LS-100 drive, flash memory card, or memory stick. The disk storage 1624 also can include storage media separately or in combination with other storage media including, but not limited to, an optical disk drive such as a compact disk ROM device (CD-ROM), CD recordable drive (CD-R Drive), CD rewritable drive (CD-RW Drive) or a digital versatile disk ROM drive (DVD-ROM). To facilitate connection of the disk storage 1624 to the system bus 1618, a removable or non-removable interface can be used, such as interface 1626. FIG. 16 also depicts software that can act as an intermediary between users and the basic computer resources described in the suitable operating environment 1600. Such software can also include, for example, an operating system 1628. Operating system 1628, which can be stored on disk storage 1624, acts to control and allocate resources of the computer 1612. System applications 1630 can take advantage of the management of resources by operating system 1628 through program modules 1632 and program data 1634, e.g., stored either in system memory 1616 or on disk storage 1624. It is to be appreciated that this disclosure can be implemented with various operating systems or combinations of operating systems. A user enters commands or information into the computer 1612 through one or more input devices 1636. Input devices 1636 can include, but are not limited to, a pointing device such as a mouse, trackball, stylus, touch pad, keyboard, microphone, joystick, game pad, satellite dish, scanner, TV tuner card, digital camera, digital video camera, web camera, and the like. These and other input devices can connect to the processing unit 1614 through the system bus 1618 via one or more interface ports 1638. The one or more Interface ports 1638 can include, for example, a serial port, a parallel port, a game port, and a universal serial bus (USB). One or more output devices 1640 can use some of the same type of ports as input device 1636. Thus, for example, a USB port can be used to provide input to computer 1612, and to output information from computer 1612 to an output device 1640. Output adapter 1642 can be provided to illustrate that there are some output devices 1640 like monitors, speakers, and printers, among other output devices 1640, which require special adapters. The output adapters 1642 can include, by way of illustration and not limitation, video and sound cards that provide a means of connection between the output device 1640 and the system bus 1618. It should be noted that other devices and/or systems of devices provide both input and output capabilities such as one or more remote computers 1644.

Computer 1612 can operate in a networked environment using logical connections to one or more remote computers, such as remote computer 1644. The remote computer 1644 can be a computer, a server, a router, a network PC, a workstation, a microprocessor based appliance, a peer device or other common network node and the like, and typically can also include many or all of the elements described relative to computer 1612. For purposes of brevity, only a memory storage device 1646 is illustrated with remote computer 1644. Remote computer 1644 can be logically connected to computer 1612 through a network interface 1648 and then physically connected via communication connection 1650. Further, operation can be distributed across multiple (local and remote) systems. Network interface 1648 can encompass wire and/or wireless communication networks such as local-area networks (LAN), wide-area networks (WAN), cellular networks, etc. LAN technologies include Fiber Distributed Data Interface (I-DDI), Copper Distributed Data Interface (CDDI), Ethernet, Token Ring and the like. WAN technologies include, but are not limited to, point-to-point links, circuit switching networks like Integrated Services Digital Networks (ISDN) and variations thereon, packet switching networks, and Digital Subscriber Lines (DSL). One or more communication connections 1650 refers to the hardware/software employed to connect the network interface 1648 to the system bus 1618. While communication connection 1650 is shown for illustrative clarity inside computer 1612, it can also be external to computer 1612. The hardware/software for connection to the network interface 1648 can also include, for exemplary purposes only, internal and external technologies such as, modems including regular telephone grade modems, cable modems and DSL modems, ISDN adapters, and Ethernet cards.

Embodiments of the present invention can be a system, a method, an apparatus and/or a computer program product at any possible technical detail level of integration. The computer program product can include a computer readable storage medium (or media) having computer readable program instructions thereon for causing a processor to carry out aspects of the present invention. The computer readable storage medium can be a tangible device that can retain and store instructions for use by an instruction execution device. The computer readable storage medium can be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium can also include the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network can include copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device. Computer readable program instructions for carrying out operations of various aspects of the present invention can be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions can execute entirely on the user's computer, partly on the user's computer, as a stand-alone software package, partly on the user's computer and partly on a remote computer or entirely on the remote computer or server. In the latter scenario, the remote computer can be connected to the user's computer through any type of network, including a local area network (LAN) or a wide area network (WAN), or the connection can be made to an external computer (for example, through the Internet using an Internet Service Provider). In some embodiments, electronic circuitry including, for example, programmable logic circuitry, field-programmable gate arrays (FPGA), or programmable logic arrays (PLA) can execute the computer readable program instructions by utilizing state information of the computer readable program instructions to customize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions. These computer readable program instructions can be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions can also be stored in a computer readable storage medium that can direct a computer, a programmable data processing apparatus, and/or other devices to function in a particular manner, such that the computer readable storage medium having instructions stored therein includes an article of manufacture including instructions which implement aspects of the function/act specified in the flowchart and/or block diagram block or blocks. The computer readable program instructions can also be loaded onto a computer, other programmable data processing apparatus, or other device to cause a series of operational acts to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams can represent a module, segment, or portion of instructions, which includes one or more executable instructions for implementing the specified logical function(s). In some alternative implementations, the functions noted in the blocks can occur out of the order noted in the Figures. For example, two blocks shown in succession can, in fact, be executed substantially concurrently, or the blocks can sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

While the subject matter has been described above in the general context of computer-executable instructions of a computer program product that runs on a computer and/or computers, those skilled in the art will recognize that this disclosure also can or can be implemented in combination with other program modules. Generally, program modules include routines, programs, components, data structures, etc. that perform particular tasks and/or implement particular abstract data types. Moreover, those skilled in the art will appreciate that the inventive computer-implemented methods can be practiced with other computer system configurations, including single-processor or multiprocessor computer systems, mini-computing devices, mainframe computers, as well as computers, hand-held computing devices (e.g., PDA, phone), microprocessor-based or programmable consumer or industrial electronics, and the like. The illustrated aspects can also be practiced in distributed computing environments where tasks are performed by remote processing devices that are linked through a communications network. However, some, if not all aspects of this disclosure can be practiced on stand-alone computers. In a distributed computing environment, program modules can be located in both local and remote memory storage devices.

As used in this application, the terms "component," "system," "platform," "interface," and the like, can refer to and/or can include a computer-related entity or an entity related to an operational machine with one or more specific functionalities. The entities disclosed herein can be either hardware, a combination of hardware and software, software, or software in execution. For example, a component can be, but is not limited to being, a process running on a processor, a processor, an object, an executable, a thread of execution, a program, and/or a computer. By way of illustration, both an application running on a server and the server can be a component. One or more components can reside within a process and/or thread of execution and a component can be localized on one computer and/or distributed between two or more computers. In another example, respective components can execute from various computer readable media having various data structures stored thereon. The components can communicate via local and/or remote processes such as in accordance with a signal having one or more data packets (e.g., data from one component interacting with another component in a local system, distributed system, and/or across a network such as the Internet with other systems via the signal). As another example, a component can be an apparatus with specific functionality provided by mechanical parts operated by electric or electronic circuitry, which is operated by a software or firmware application executed by a processor. In such a case, the processor can be internal or external to the apparatus and can execute at least a part of the software or firmware application. As yet another example, a component can be an apparatus that provides specific functionality through electronic components without mechanical parts, wherein the electronic components can include a processor or other means to execute software or firmware that confers at least in part the functionality of the electronic components. In an aspect, a component can emulate an electronic component via a virtual machine, e.g., within a cloud computing system.

In addition, the term "or" is intended to mean an inclusive "or" rather than an exclusive "or." That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. Moreover, articles "a" and "an" as used in the subject specification and annexed drawings should generally be construed to mean "one or more" unless specified otherwise or clear from context to be directed to a singular form. As used herein, the terms "example" and/or "exemplary" are utilized to mean serving as an example, instance, or illustration. For the avoidance of doubt, the subject matter disclosed herein is not limited by such examples. In addition, any aspect or design described herein as an "example" and/or "exemplary" is not necessarily to be construed as preferred or advantageous over other aspects or designs, nor is it meant to preclude equivalent exemplary structures and techniques known to those of ordinary skill in the art.

As it is employed in the subject specification, the term "processor" can refer to substantially any computing processing unit or device including, but not limited to, single-core processors; single-processors with software multithread execution capability; multi-core processors; multi-core processors with software multithread execution capability; multi-core processors with hardware multithread technology; parallel platforms; and parallel platforms with distributed shared memory. Additionally, a processor can refer to an integrated circuit, an application specific integrated circuit (ASIC), a digital signal processor (DSP), a field programmable gate array (FPGA), a programmable logic controller (PLC), a complex programmable logic device (CPLD), a discrete gate or transistor logic, discrete hardware components, or any combination thereof designed to perform the functions described herein. Further, processors can exploit nano-scale architectures such as, but not limited to, molecular and quantum-dot based transistors, switches and gates, in order to optimize space usage or enhance performance of user equipment. A processor can also be implemented as a combination of computing processing units. In this disclosure, terms such as "store," "storage," "data store," data storage," "database," and substantially any other information storage component relevant to operation and functionality of a component are utilized to refer to "memory components," entities embodied in a "memory," or components including a memory. It is to be appreciated that memory and/or memory components described herein can be either volatile memory or nonvolatile memory, or can include both volatile and nonvolatile memory. By way of illustration, and not limitation, nonvolatile memory can include read only memory (ROM), programmable ROM (PROM), electrically programmable ROM (EPROM), electrically erasable ROM (EEPROM), flash memory, or non-volatile random access memory (RAM) (e.g., ferroelectric RAM (FeRAM). Volatile memory can include RAM, which can act as external cache memory, for example. By way of illustration and not limitation, RAM is available in many forms such as synchronous RAM (SRAM), dynamic RAM (DRAM), synchronous DRAM (SDRAM), double data rate SDRAM (DDR SDRAM), enhanced SDRAM (ESDRAM), Synchlink DRAM (SLDRAM), direct Rambus RAM (DRRAM), direct Rambus dynamic RAM (DRDRAM), and Rambus dynamic RAM (RDRAM). Additionally, the disclosed memory components of systems or computer-implemented methods herein are intended to include, without being limited to including, these and any other suitable types of memory.

What has been described above include mere examples of systems, computer program products and computer-implemented methods. It is, of course, not possible to describe every conceivable combination of components, products and/or computer-implemented methods for purposes of describing this disclosure, but one of ordinary skill in the art can recognize that many further combinations and permutations of this disclosure are possible. Furthermore, to the extent that the terms "includes," "has," "possesses," and the like are used in the detailed description, claims, appendices and drawings such terms are intended to be inclusive in a manner similar to the term "comprising" as "comprising" is interpreted when employed as a transitional word in a claim. The descriptions of the various embodiments have been presented for purposes of illustration, but are not intended to be exhaustive or limited to the embodiments disclosed.

What is claimed is:

1. An apparatus, comprising:
a housing; and
a microfluidic chip contained within the housing, wherein the microfluidic chip comprises:
a separation unit comprising nanoscale deterministic lateral displacement arrays in fluid communication with an inlet bus formed around a perimeter of a first side of the nanoscale deterministic displacement arrays;
an outlet bus comprising an etched channel formed on a second side of the nanoscale deterministic displacement arrays opposite the first side within a thickness of the microfluidic chip, wherein the nanoscale deterministic displacement arrays are configured to laterally displace particles of interest comprised within a sample fluid supplied from the inlet bus and direct the particles of interest into the outlet bus; and
a detection unit configured for detecting presence of one or more biomarkers associated with the particles of interest using one or more detection molecules or macromolecules that chemically reacts with the one or more biomarkers, wherein the outlet bus surrounds the detection unit and supplies the particles of interest onto a sensing element surface of the detection unit coated with one or more detection molecules or macromolecules.

2. The apparatus of claim 1, wherein the particles of interest comprise exosomes.

3. The apparatus of claim 1, wherein the particles of interest have a diameter size from about 10.0 nanometers to about 200 nanometers.

4. The apparatus of claim 1, wherein the one or more detection molecules or macromolecules comprise an antibody or aptamer that binds with a target epitope of the one or more biomarkers.

5. The apparatus of claim 1, wherein the sensing element surface comprises a signal enhancing structure selected from a group consisting of a photonic grating structure, a photonic pillar array structure, an optoelectrical structure, and a plasmonic structure.

6. The apparatus of claim 1, wherein the one or more detection molecules or macromolecules chemically react with the one or more biomarkers by binding to the one or more detection molecules or macromolecules, and wherein based on the binding, the one or more detection molecules or macromolecules generate a visual signal.

7. The apparatus of claim 6, wherein a portion of the housing formed adjacent to the sensing element surface is transparent or partially transparent and enables visual observation of the visual signal.

8. The apparatus of claim 1, wherein the detection unit further comprises:
an injection channel formed around a perimeter of the sensing element surface and in fluid communication with the outlet bus that uniformly supplies the particles of interest onto the sensing element surface.

9. The apparatus of claim 1, wherein the detection unit further comprises:
at least one inlet via in fluid communication with the sensing element surface via which detection fluid comprising the one or more detection molecules or macromolecules is introduced onto the sensing element surface to coat the sensing element surface with the one or more detection molecules or macromolecules.

10. The apparatus of claim 1, wherein the outlet bus supplies the particles of interest onto the sensing element surface within a stream of buffer fluid, and wherein the detection unit further comprises:
a central outlet located in a center region of the sensing element surface via which the buffer fluid, and unreacted portions of the target biological entities that fail to chemically react with the one or more detection molecules or macromolecules, are excreted from the detection unit.

11. The apparatus of claim 9, wherein the detection unit further comprises:
a blocking element formed at an interface between the sensing element surface and the at least one inlet, wherein the blocking element inhibits reverse flow of one or more reacted molecular complexes from the sensing element surface through the at least one inlet, wherein the one or more reacted molecular complexes are formed as a result of a chemical reaction between the one or more detection molecules or macromolecules and the one or more biomarkers.

12. The apparatus of claim 1, wherein the detection unit comprises two or more separate detection chambers, wherein respective chambers of the two or more separate detection chambers comprise different types of detection molecules or macromolecules of the one or more detection molecules or macromolecules, and wherein the different types of detection molecules or macromolecules chemically react with different types of biomarkers of the one or more biomarkers.

13. A method comprising:
isolating target particles having a defined size range from other particles included in a biological fluid sample using a separation unit comprising nanoscale deterministic lateral displacement arrays formed on a microfluidic chip in fluid communication with an inlet bus formed around a perimeter of a first side of the nanoscale deterministic displacement arrays;
collecting, as a result of the isolating, the target particles in an outlet bus comprising an etched channel formed on a second side of the nanoscale deterministic displacement arrays opposite the first side within a thickness of the microfluidic chip;
driving flow of a buffer fluid comprising the target particles from the outlet bus to a sensing element formed on the microfluidic chip, wherein the outlet bus surrounds the sensing element; and
facilitating detection of presence of one or more biomarkers associated with the target particles based on whether a detectable signal is generated at the sensing element in response to the driving.

14. The method of claim 13, wherein the target particles comprise exosomes.

15. The method of claim 13, wherein the sensing element comprises one or more detection molecules or macromolecules and wherein the detectable signal comprises a reaction signal that is indicative of a chemical interaction between the one or more detection molecules or macromolecules and the one or more biomarkers.

16. The method of claim 15, wherein the chemical interaction is selected from a group consisting of: a covalent bonding reaction, an electrostatic interaction, a hydrophobic interaction, an antibody-epitope interaction, an aptamer-epitope reaction, a protein-protein interaction, a protein-small molecule interaction, a polymerization reaction, a complementarity reaction, a complementary deoxyribonucleic acid (DNA) strand hybridization interaction, and a complementary ribonucleic acid (RNA) strand hybridization interaction.

17. The method of claim 15, wherein the method further comprises:
prior to the driving, functionalizing a surface of the sensing element with the one or more detection molecules or macromolecules, wherein the functionalizing comprises injecting a solution comprising the one or more detection molecules or macromolecules into a chamber enclosing the surface of sensing element via at least one injection inlet of the microfluidic chip.

18. The method of claim 13, wherein the detectable signal comprises a visual signal and wherein the method further comprises:
determining whether the detectable signal is generated using a microscope positioned adjacent the sensing element.

19. The method of claim 13, wherein the detectable signal comprises a visual signal and wherein the method further comprises:
capturing, by a device operatively coupled to a processor, image data of the sensing element in association with the driving; and determining, by the device, whether the visual signal is generated based on the image data.

20. An apparatus, comprising:
a housing; and
a microfluidic chip contained within the housing, wherein the microfluidic chip comprises:
  a separation unit comprising nanoscale deterministic lateral displacement arrays in fluid communication with an inlet bus formed around a perimeter of a first side of the nanoscale deterministic displacement arrays;
  an outlet bus comprising an etched channel formed on a second side of the nanoscale deterministic displacement arrays opposite the first side within a thickness of the microfluidic chip, wherein the nanoscale deterministic displacement arrays are configured to laterally displace exosomes comprised within a sample fluid supplied from the inlet bus and direct the exosomes into the outlet bus; and
  a detection unit configured for detecting presence of different biomarkers located on or within with the exosomes using different detection entities located on sensing surface of the detection unit that respectively chemically react with the different biomarkers, wherein the different detection entities are selected from a group consisting of molecules and macromolecules, and wherein the outlet bus surrounds the sensing surface and supplies the exosomes to the sensing surface.

21. The apparatus of claim 20, wherein the detection unit comprises different chambers that respectively detect presence of a different type of biomarker of the different types of biomarkers, and wherein the different chambers are respectively coated with a different detection entity of the different detection entities.

22. A system, comprising:
a microfluidic chip contained within a housing, wherein the microfluidic chip comprises:
  a separation unit comprising nanoscale deterministic lateral displacement arrays in fluid communication with an inlet bus formed around a perimeter of a first side of the nanoscale deterministic displacement arrays;
  an outlet bus comprising an etched channel formed on a second side of the nanoscale deterministic displacement arrays opposite the first side within a thickness of the microfluidic chip, wherein the nanoscale deterministic displacement arrays are configured to laterally displace particles of interest comprised within a biological sample fluid supplied from the inlet bus and direct the particles of interest into the outlet bus within a stream of buffer fluid; and
  a detection unit configured for detecting presence of one or more biomarkers associated with the particles of interest using one or more detection molecules or macromolecules that chemically react with the one or more biomarkers, wherein the outlet bus surrounds the detection unit and supplies the stream of buffer fluid onto a sensing element surface of the detection unit coated with one or more detection molecules or macromolecules; and
an imaging device that captures image data in association with flow of the stream of buffer fluid onto the sensing element and contact of the stream of buffer fluid with the one or more detection molecules or macromolecules.

23. The system of claim 22, further comprising:
a memory that stores computer executable components; and
a processor that executes the computer executable components stored in the memory, wherein the computer executable components comprise:
  an analysis component that evaluates the image data to determine biomarker information regarding the presence of the one or more biomarkers; and
  a diagnosis component that determines diagnostic information regarding a medical condition of a patient from which the biological fluid is sampled from based on the biomarker information.

* * * * *